(12) United States Patent
Ouyang

(10) Patent No.: US 12,268,358 B2
(45) Date of Patent: Apr. 8, 2025

(54) PORTABLE ENDOSCOPE WITH SIDE-MOUNTABLE DISPOSABLE PORTION

(71) Applicant: UroViu, Corp., Bellevue, WA (US)

(72) Inventor: Xiaolong Ouyang, Bellevue, WA (US)

(73) Assignee: UroViu Corp., Bellevue, WA (US)

( * ) Notice: Subject to any disclaimer, the term of this patent is extended or adjusted under 35 U.S.C. 154(b) by 697 days.

(21) Appl. No.: 17/349,674

(22) Filed: Jun. 16, 2021

(65) Prior Publication Data

US 2021/0307591 A1 Oct. 7, 2021

Related U.S. Application Data

(63) Continuation-in-part of application No. 16/664,082, filed on Dec. 5, 2019, now Pat. No. 11,071,442.

(51) Int. Cl.
*A61B 1/00* (2006.01)
*A61B 1/05* (2006.01)
*A61B 1/06* (2006.01)

(52) U.S. Cl.
CPC ...... *A61B 1/00103* (2013.01); *A61B 1/00016* (2013.01); *A61B 1/00048* (2013.01); *A61B 1/00052* (2013.01); *A61B 1/00066* (2013.01); *A61B 1/00105* (2013.01); *A61B 1/00124* (2013.01); *A61B 1/05* (2013.01); *A61B 1/06* (2013.01)

(58) Field of Classification Search
CPC ....... A61B 1/00105; A61B 1/05; A61B 1/015; A61B 1/018; A61B 1/00066; A61B 1/00103; A61B 1/00048; A61B 1/00034
See application file for complete search history.

(56) References Cited

U.S. PATENT DOCUMENTS

| 4,854,302 A | 8/1989 | Allred, III |
| 4,979,497 A | 12/1990 | Matsura |

(Continued)

FOREIGN PATENT DOCUMENTS

| CN | 102858275 | 1/2013 |
| CN | 105636621 | 6/2016 |

(Continued)

OTHER PUBLICATIONS

International Search Report and Written Opinion for PCT/US20/046018, mailed Oct. 29, 2020.

(Continued)

*Primary Examiner* — Alexandra L Newton
(74) *Attorney, Agent, or Firm* — Wissing Miller LLP

(57) ABSTRACT

A handheld endoscope has a disposable, single-use portion that includes a distal tip, cannula, housings, and a proximal port that is connected to a substantially straight working channel. The cannula is rotatable about the main longitudinal axis of the cannula. The endoscope also includes a re-usable portion that has a handle and display module. The single-use and re-usable portions mate and un-mate with each other via physical side-mounting arrangement as well as separate electrical connectors. The handle can house imaging system electronics that support manual and auto imaging modes which can be selected via touch screen control on the display module. The re-useable portion is sealed with various o-rings and/or gaskets and can be highly fluid resistant to facilitate disinfecting and/or sterilization.

9 Claims, 16 Drawing Sheets

(56) References Cited

U.S. PATENT DOCUMENTS

| | | |
|---|---|---|
| 5,010,876 A | 4/1991 | Henley |
| 5,188,093 A | 2/1993 | Lafferty |
| 5,237,984 A | 8/1993 | Williams, II |
| 5,281,214 A | 1/1994 | Wilkins |
| 5,323,767 A | 6/1994 | Lafferty |
| 5,329,936 A | 7/1994 | Lafferty |
| 5,474,057 A | 12/1995 | Makower |
| 5,486,155 A | 1/1996 | Muller |
| 5,527,332 A | 6/1996 | Clement |
| 5,549,547 A | 8/1996 | Cohen |
| 5,569,163 A | 10/1996 | Francis |
| 5,578,030 A | 11/1996 | Levin |
| 5,666,561 A | 9/1997 | Stephenson |
| 5,667,472 A | 9/1997 | Finn |
| 5,667,476 A | 9/1997 | Frassica et al. |
| 5,785,644 A | 7/1998 | Grabover |
| 5,860,953 A | 1/1999 | Snoke |
| 5,873,814 A | 2/1999 | Adair |
| 5,895,361 A | 4/1999 | Turturro |
| 5,928,137 A | 7/1999 | Green |
| 5,935,141 A | 8/1999 | Weldon |
| 5,957,947 A | 9/1999 | Wattiez |
| 6,007,531 A | 12/1999 | Snoke |
| 6,007,546 A | 12/1999 | Snow |
| 6,017,322 A | 1/2000 | Snoke |
| 6,033,378 A | 3/2000 | Lundquist |
| 6,059,719 A | 5/2000 | Yamamato et al. |
| 6,095,970 A | 8/2000 | Hidaka |
| 6,174,307 B1 | 1/2001 | Daniel |
| 6,210,416 B1 | 4/2001 | Chu |
| 6,211,904 B1 | 4/2001 | Adair |
| 6,221,007 B1 | 4/2001 | Green |
| 6,221,070 B1 | 4/2001 | Tu et al. |
| 6,261,226 B1 | 7/2001 | McKenna |
| 6,280,386 B1 | 8/2001 | Alfano |
| 6,331,174 B1 | 12/2001 | Reinhard |
| 6,387,043 B1 | 5/2002 | Yoon |
| 6,398,743 B1 | 6/2002 | Halseth |
| 6,507,699 B2 | 1/2003 | Lemoine |
| 6,518,823 B1 | 2/2003 | Kawai |
| 6,673,087 B1 | 1/2004 | Chang |
| 6,793,882 B1 | 9/2004 | Verschuur |
| 6,917,380 B1 | 7/2005 | Tay |
| 7,256,446 B2 | 8/2007 | Hu |
| 7,428,378 B1 | 9/2008 | Warpakowski |
| 7,507,205 B2 | 3/2009 | Borovsky |
| 7,591,799 B2 | 9/2009 | Selkee |
| 7,606,609 B2 | 10/2009 | Muranushi |
| 7,780,650 B2 | 8/2010 | Frassica |
| 7,798,995 B2 | 9/2010 | Yue |
| 7,931,616 B2 | 4/2011 | Selkee |
| 7,946,981 B1 | 5/2011 | Cubb |
| 8,057,464 B2 | 9/2011 | Chen |
| 8,052,609 B2 | 11/2011 | Harhen |
| 8,187,171 B2 | 5/2012 | Irion |
| 8,197,398 B2 | 6/2012 | Scholly |
| 8,235,975 B2 | 8/2012 | Chen |
| 8,361,775 B2 | 4/2013 | Flower |
| 8,460,182 B2 | 6/2013 | Ouyang |
| 8,523,808 B2 | 9/2013 | Selkee |
| 8,696,552 B2 | 4/2014 | Whitman |
| 8,803,960 B2 | 8/2014 | Sonnenschein |
| 8,834,357 B2 | 9/2014 | Oskin |
| 8,845,522 B2 | 9/2014 | McIntyre |
| 8,952,312 B2 | 2/2015 | Blanqart |
| 8,998,844 B2 | 4/2015 | Reed |
| 9,649,014 B2 | 5/2017 | Ouyang |
| 9,736,342 B2 | 8/2017 | Mueckl |
| 9,895,048 B2 | 2/2018 | Ouyang |
| 10,278,563 B2 | 5/2019 | Ouyang |
| 10,292,571 B2 | 5/2019 | Ouyang |
| 10,595,710 B2 | 3/2020 | Gill |
| 2001/0007051 A1 | 7/2001 | Nakashima |
| 2001/0049509 A1 | 12/2001 | Sekine |
| 2003/0016284 A1 | 1/2003 | Squilla |
| 2003/0023142 A1 | 1/2003 | Grabover |
| 2003/0078476 A1 | 4/2003 | Hill |
| 2003/0078502 A1 | 4/2003 | Miyaki |
| 2003/0151680 A1 | 8/2003 | McDermott |
| 2003/0199735 A1 | 10/2003 | Dickopp |
| 2004/0054254 A1 | 3/2004 | Miyake |
| 2004/0054259 A1 | 3/2004 | Hasegawa |
| 2004/0138558 A1 | 7/2004 | Dunki-Jacobs |
| 2004/0162572 A1 | 8/2004 | Sauer |
| 2005/0010178 A1 | 1/2005 | Katz |
| 2005/0264687 A1 | 1/2005 | Murayama |
| 2005/0049459 A1 | 3/2005 | Hern |
| 2005/0065397 A1 | 3/2005 | Saadat |
| 2005/0085695 A1 | 4/2005 | Sherner |
| 2005/0154262 A1 | 7/2005 | Banik |
| 2005/0159646 A1 | 7/2005 | Nordstrom |
| 2005/0177027 A1 | 8/2005 | Hirata |
| 2005/0277874 A1 | 12/2005 | Selkee |
| 2005/0277875 A1 | 12/2005 | Selkee |
| 2006/0052710 A1 | 3/2006 | Miura |
| 2006/0063976 A1 | 3/2006 | Aizenfeld |
| 2006/0114986 A1 | 6/2006 | Knapp |
| 2006/0152601 A1 | 7/2006 | Parekh |
| 2006/0167340 A1 | 7/2006 | Peas |
| 2006/0171693 A1 | 8/2006 | Todd |
| 2006/0173245 A1 | 8/2006 | Todd |
| 2006/0184227 A1 | 8/2006 | Rust |
| 2006/0259124 A1 | 11/2006 | Matsuoka |
| 2006/0287576 A1 | 12/2006 | Tsuji |
| 2007/0060789 A1 | 3/2007 | Uchimura |
| 2007/0081920 A1 | 4/2007 | Murphy |
| 2007/0117437 A1 | 5/2007 | Boehnlein |
| 2007/0129604 A1 | 6/2007 | Hatcher |
| 2007/0162095 A1 | 7/2007 | Kimmel |
| 2007/0167678 A1 | 7/2007 | Moskowitz |
| 2007/0167868 A1 | 7/2007 | Sauer |
| 2007/0173693 A1 | 7/2007 | Refael |
| 2007/0187875 A1 | 8/2007 | Terasaki |
| 2007/0188604 A1 | 8/2007 | Miyamoto |
| 2007/0197875 A1 | 8/2007 | Osaka |
| 2007/0210162 A1 | 9/2007 | Keen |
| 2007/0225556 A1 | 9/2007 | Ortiz |
| 2007/0238927 A1 | 10/2007 | Ueno |
| 2007/0249904 A1 | 10/2007 | Amano |
| 2008/0004642 A1 | 1/2008 | Birk |
| 2008/0071144 A1 | 3/2008 | Kimmel |
| 2008/0097550 A1 | 4/2008 | Dicks |
| 2008/0108869 A1 | 5/2008 | Sanders |
| 2008/0195125 A1 | 8/2008 | Orbay |
| 2008/0195128 A1 | 8/2008 | Orbay |
| 2008/0225410 A1 | 9/2008 | Ning |
| 2008/0234547 A1 | 9/2008 | Irion et al. |
| 2008/0255416 A1 | 10/2008 | Gilboa |
| 2008/0262306 A1 | 10/2008 | Kawai |
| 2008/0300456 A1 | 12/2008 | Irion |
| 2009/0027489 A1 | 1/2009 | Takemura |
| 2009/0065565 A1 | 3/2009 | Lemoine |
| 2009/0076321 A1 | 3/2009 | Suyama |
| 2009/0076328 A1 | 3/2009 | Root |
| 2009/0080214 A1 | 3/2009 | Watanabe |
| 2009/0105538 A1 | 4/2009 | Van Dam |
| 2009/0118580 A1 | 5/2009 | Sun |
| 2009/0118641 A1 | 5/2009 | Van Dam |
| 2009/0149713 A1 | 7/2009 | Niida |
| 2009/0225159 A1 | 9/2009 | Schneider |
| 2009/0227897 A1 | 9/2009 | Wendt |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |

(56) References Cited

U.S. PATENT DOCUMENTS

| | | | |
|---|---|---|---|
| 2010/0026201 A1 | 10/2010 | Frangioni | |
| 2011/0009694 A1* | 1/2011 | Schultz | A61B 10/0233 600/109 |
| 2011/0034769 A1 | 2/2011 | Adair | |
| 2011/0037876 A1 | 2/2011 | Talbert | |
| 2011/0054446 A1 | 3/2011 | Schultz | |
| 2011/0092775 A1 | 4/2011 | Deshmukh | |
| 2011/0105839 A1 | 5/2011 | Hoffman | |
| 2011/0112622 A1 | 5/2011 | Phan | |
| 2011/0124961 A1 | 5/2011 | Zimmon | |
| 2011/0130627 A1 | 6/2011 | McGrail | |
| 2011/0211115 A1 | 9/2011 | Tsai | |
| 2011/0213206 A1 | 9/2011 | Boutillette | |
| 2011/0245602 A1 | 10/2011 | Brannon | |
| 2011/0264191 A1 | 10/2011 | Rothstein | |
| 2011/0288482 A1 | 11/2011 | Farrell | |
| 2011/0313245 A1 | 12/2011 | Scholly | |
| 2012/0016191 A1 | 1/2012 | Ito | |
| 2012/0040305 A1 | 2/2012 | Karazivan | |
| 2012/0041533 A1 | 2/2012 | Bertolino | |
| 2012/0053515 A1 | 3/2012 | Crank | |
| 2012/0100729 A1 | 4/2012 | Edidin | |
| 2012/0165916 A1 | 6/2012 | Jordan | |
| 2012/0178991 A1 | 7/2012 | Clark | |
| 2012/0226103 A1 | 9/2012 | Gunday | |
| 2012/0236138 A1 | 9/2012 | Liu | |
| 2012/0245242 A1 | 9/2012 | Peiffer | |
| 2012/0245418 A1 | 9/2012 | Boulais | |
| 2012/0253116 A1 | 10/2012 | Sniffin | |
| 2012/0259203 A1 | 10/2012 | Devereux | |
| 2012/0286020 A1 | 11/2012 | Smith | |
| 2012/0289858 A1 | 11/2012 | Ouyang | |
| 2013/0006145 A1 | 1/2013 | Toomey | |
| 2013/0035553 A1 | 2/2013 | Kongstorum | |
| 2013/0046142 A1 | 2/2013 | Remijan | |
| 2013/0057667 A1 | 5/2013 | McGrath | |
| 2013/0150672 A1 | 6/2013 | Fujitani | |
| 2013/0172676 A1 | 7/2013 | Levy | |
| 2013/0190561 A1 | 7/2013 | Oskin | |
| 2013/0225921 A1 | 8/2013 | Liu | |
| 2013/0253402 A1 | 9/2013 | Badawi | |
| 2013/0096378 A1 | 10/2013 | Alexander | |
| 2013/0289559 A1 | 10/2013 | Reid | |
| 2013/0324973 A1 | 12/2013 | Reed | |
| 2013/0345514 A1 | 12/2013 | Manion | |
| 2014/0022649 A1 | 1/2014 | Echhardt | |
| 2014/0107416 A1 | 4/2014 | Bimkrant | |
| 2014/0111634 A1 | 4/2014 | Mueckl | |
| 2014/0154399 A1 | 6/2014 | Weikart | |
| 2014/0180007 A1 | 6/2014 | Edidin | |
| 2014/0188211 A1 | 7/2014 | Roeder | |
| 2014/0213848 A1 | 7/2014 | Moskowitz | |
| 2014/0228635 A1 | 8/2014 | Tuliakov | |
| 2014/0275763 A1 | 9/2014 | King | |
| 2014/0296866 A1 | 10/2014 | Salman | |
| 2014/0323991 A1 | 10/2014 | Tang | |
| 2015/0005575 A1 | 1/2015 | Kobayashi | |
| 2015/0011830 A1 | 1/2015 | Hunter | |
| 2015/0018622 A1 | 1/2015 | Tesar | |
| 2015/0018710 A1 | 1/2015 | Furlong | |
| 2015/0150441 A1 | 6/2015 | Ouyang | |
| 2015/0164313 A1 | 6/2015 | Oyuang | |
| 2015/0196197 A1 | 7/2015 | Kienzle | |
| 2015/0238175 A1 | 8/2015 | Seiger | |
| 2015/0238251 A1 | 8/2015 | Shikhman | |
| 2015/0297311 A1 | 10/2015 | Tesar | |
| 2016/0073853 A1 | 3/2016 | Venkatesan et al. | |
| 2016/0077008 A1 | 3/2016 | Takasu | |
| 2016/0174819 A1 | 6/2016 | Ouyang | |
| 2016/0334694 A1 | 11/2016 | Liu | |
| 2016/0367119 A1 | 12/2016 | Ouyang | |
| 2017/0086651 A1 | 3/2017 | Sato | |
| 2017/0181853 A1 | 6/2017 | Rothstein | |
| 2017/0188793 A1 | 7/2017 | Ouyang | |
| 2017/0188795 A1 | 7/2017 | Ouyang | |
| 2017/0215699 A1 | 8/2017 | Ouyang | |
| 2017/0295347 A1 | 10/2017 | Schneider | |
| 2017/0310858 A1 | 10/2017 | Mueck | |
| 2018/0132700 A1* | 5/2018 | Ouyang | A61B 1/00052 |
| 2018/0184892 A1* | 7/2018 | Truckai | A61B 1/303 |
| 2018/0235441 A1 | 8/2018 | Huang | |
| 2018/0256009 A1 | 9/2018 | Ouyang | |
| 2018/0289241 A1 | 10/2018 | Zhou | |
| 2019/0029497 A1 | 1/2019 | Mirza | |
| 2019/0142262 A1 | 5/2019 | Inglis | |
| 2019/0200845 A1* | 7/2019 | Levy | A61B 90/361 |
| 2019/0216325 A1 | 7/2019 | Ouyang | |
| 2019/0223691 A1 | 7/2019 | Takatsuji | |
| 2019/0246873 A1 | 8/2019 | Lu | |
| 2019/0246884 A1 | 8/2019 | Lu et al. | |
| 2019/0282071 A1 | 9/2019 | Ouyang | |
| 2019/0282073 A1* | 9/2019 | Truckai | A61B 1/303 |
| 2019/0320879 A1 | 10/2019 | Langell | |
| 2019/0374095 A1 | 12/2019 | Lord | |
| 2020/0204776 A1 | 6/2020 | Themelis | |
| 2020/0214739 A1 | 7/2020 | Shi | |
| 2020/0275827 A1 | 9/2020 | Weise | |
| 2021/0052383 A1 | 2/2021 | Rothstein | |
| 2021/0228806 A1 | 7/2021 | Streeter | |
| 2021/0401277 A1 | 12/2021 | Ouyang | |

FOREIGN PATENT DOCUMENTS

| | | |
|---|---|---|
| CN | 106132273 | 11/2016 |
| CN | 110234265 | 9/2019 |
| EP | 1690512 | 8/2006 |
| EP | 2560589 | 4/2010 |
| EP | 3384879 | 4/2011 |
| EP | 2749258 | 7/2014 |
| EP | 3078354 | 10/2016 |
| EP | 2721992 | 4/2018 |
| JP | 2009148420 | 7/2009 |
| WO | 2011133792 | 10/2011 |
| WO | 2012060932 | 5/2012 |
| WO | 2012151073 | 11/2012 |
| WO | 2014031192 | 2/2014 |
| WO | 2014065901 | 5/2015 |
| WO | 2016032729 | 3/2016 |
| WO | 2016040131 | 3/2016 |
| WO | 2016137838 | 9/2016 |
| WO | 2018136950 | 7/2018 |
| WO | 2019237003 | 12/2019 |

OTHER PUBLICATIONS

International Search Report and Written Opinion of PCT/US2016/18670, dated Jul. 12, 2016.

International Search Report and Written Opinion of PCT/US2018/014880, dated Jun. 6, 2018.

International Search Report and Written Opinion of PCT/US2018/065396, dated Feb. 24, 2017.

International Search Report and Written Opinion of PCT/US2021/050095 dated Dec. 17, 2021.

International Search Report and Written Opinion of PCT/US2019/036060 dated Aug. 27, 2019.

International Search Report and Written Opinion of PCT/US2017/053171 mailed Dec. 5, 2017.

International Preliminary Report on Patentability of PCT/US2017/053171 completed on Jul. 1, 2019.

Extended European Search Report of European Patent Application No. EP19816177 completed Feb. 2, 2022.

Chinese Office Action for application No. 202011219896.4, dated Jan. 30, 2024.

* cited by examiner

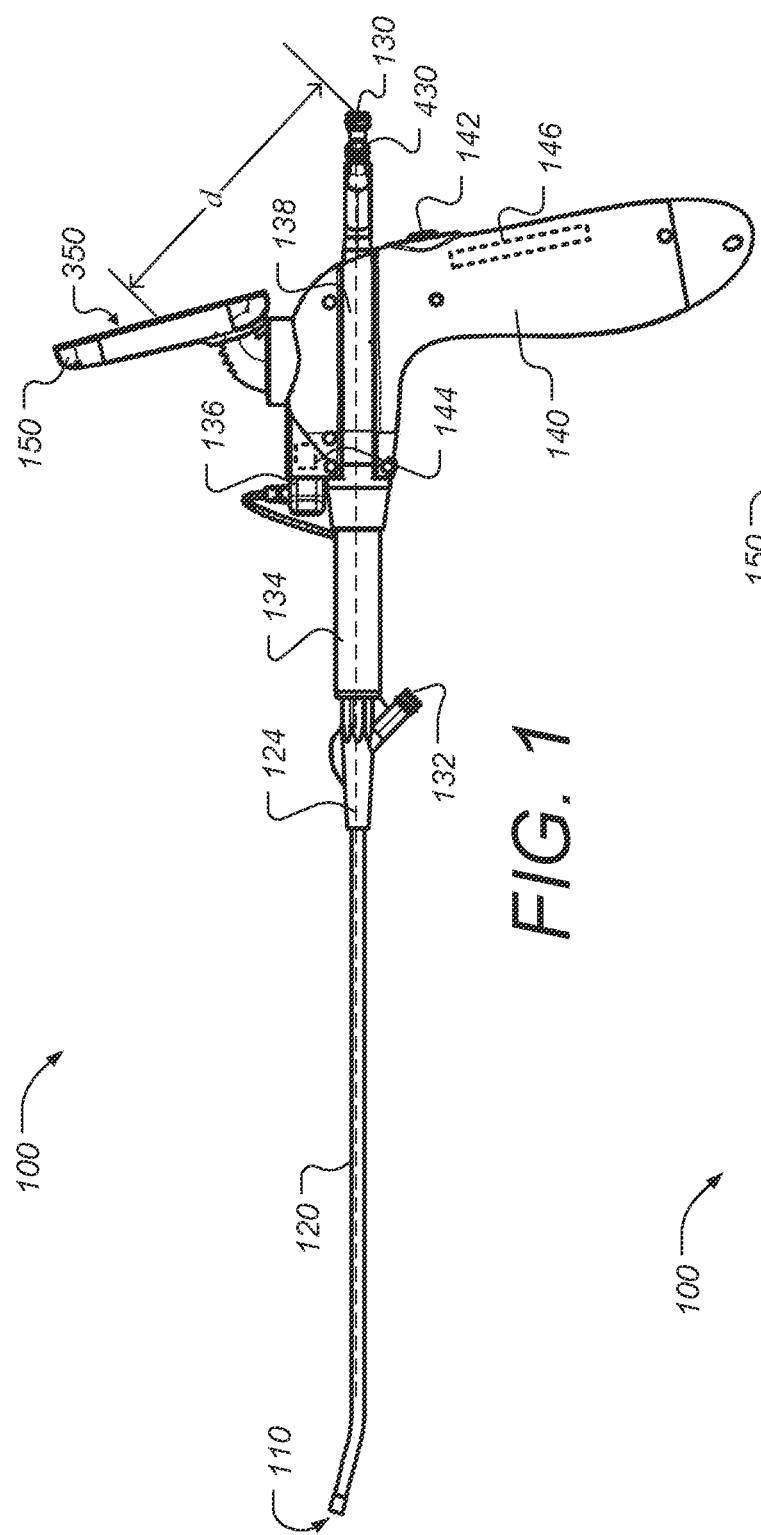
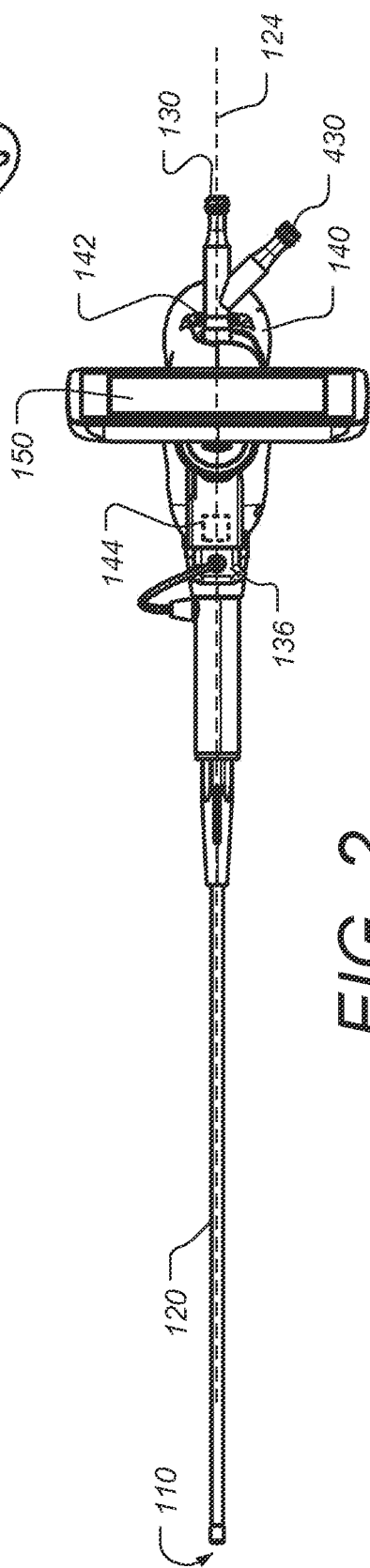

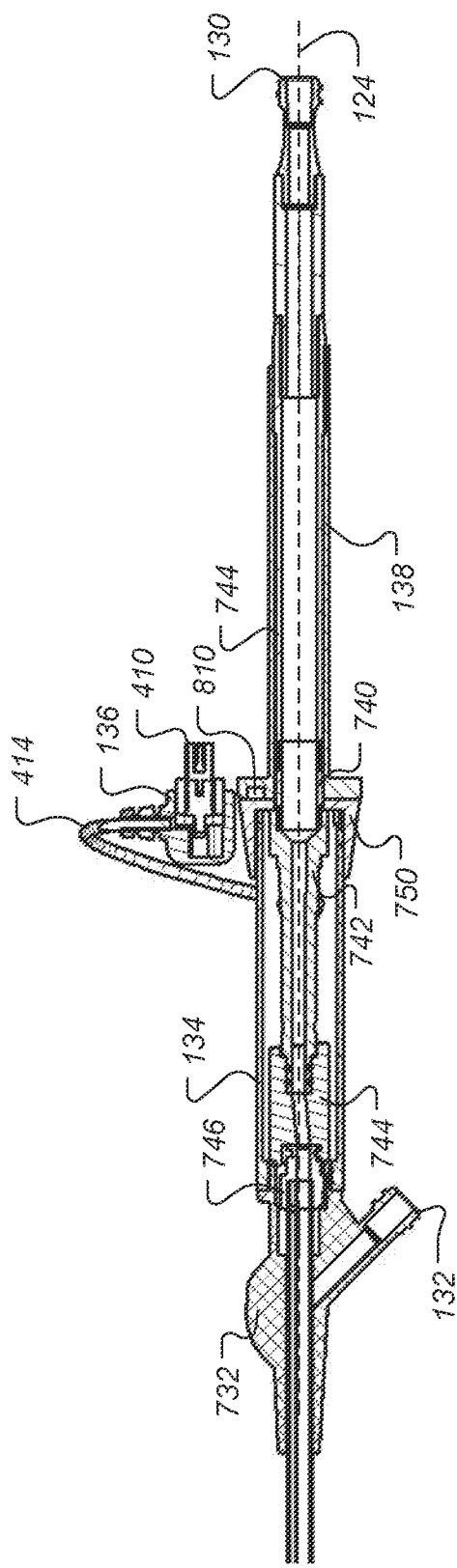
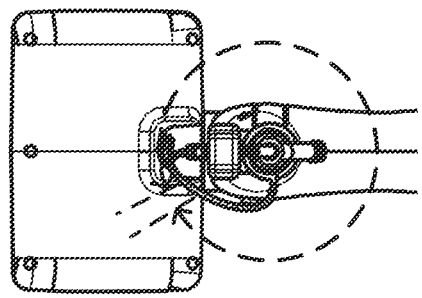
FIG. 8A
FIG. 8B

PORTABLE ENDOSCOPE WITH SIDE-MOUNTABLE DISPOSABLE PORTION

REFERENCE TO RELATED APPLICATIONS

This patent application is a continuation-in-part of parent U.S. application Ser. No. 16/664,082 filed on Dec. 5, 2019, in which a Notice of Allowance was mailed on Mar. 10, 2021. This CIP application claims the benefit of and incorporates by reference said parent application and each of the following provisional applications:

U.S. Prov. Ser. No. 63/178,136 filed Apr. 22, 2021;
U.S. Prov. Ser. No. 63/112,765 filed Nov. 12, 2020; and
U.S. Prov. Ser. No. 63/077,635 filed Sep. 13, 2020.

This patent application incorporates by reference each of the following provisional and non-provisional patent applications and issued patent(s):

U.S. Prov. Ser. No. 62/901,393 filed Sep. 17, 2019;
U.S. Prov. Ser. No. 62/897,352 filed Sep. 8, 2019
U.S. Prov. Ser. No. 62/884,688 filed Aug. 9, 2019
U.S. Prov. Ser. No. 62/880,677 filed Jul. 31, 2019
U.S. Prov. Ser. No. 62/873,861 filed Jul. 13, 2019
U.S. Prov. Ser. No. 62/870,748 filed Jul. 4, 2019
U.S. Prov. Ser. No. 62/878,384 filed Jul. 25, 2019
U.S. Prov. Ser. No. 62/842,297 filed May 2, 2019;
U.S. Prov. Ser. No. 62/825,948 filed Mar. 29, 2019;
U.S. Prov. Ser. No. 62/821,536 filed Mar. 21, 2019;
U.S. Prov. Ser. No. 62/821,430 filed Mar. 20, 2019;
U.S. Prov. Ser. No. 62/797,235 filed Jan. 26, 2019;
U.S. Prov. Ser. No. 62/796,346 filed Jan. 24, 2019;
U.S. Prov. Ser. No. 62/795,042 filed Jan. 22, 2019; and
U.S. Prov. Ser. No. 62/791,045 filed Jan. 11, 2019.
U.S. Pat. No. 9,895,048 issued Feb. 20, 2018;
U.S. Pat. No. 9,895,858 issued Feb. 20, 2018;
U.S. Pat. No. 10,278,563 issued May 7, 2019;
U.S. Pat. No. 10,292,571 issued May 21, 2019;
U.S. Ser. No. 15/856,077 filed Dec. 28, 2017;
U.S. Ser. No. 17/145,466 filed Jan. 11, 2021;
U.S. Ser. No. 16/407,028 filed May 8, 2019;
U.S. Ser. No. 16/413,160 filed May 15, 2019;
U.S. Ser. No. 15/462,331 filed Mar. 17, 2017;
U.S. Ser. No. 14/913,867 filed Feb. 23, 2016;
Int'l. Pat. App. No. PCT/US20/38349 filed Jun. 18, 2020;
Int'l. Pat. App. No. PCT/US18/14880 filed Jan. 23, 2018;
Int'l. Pat. App. No. PCT/US16/65396 filed Dec. 7, 2016;
Int'l. Pat. App. No. PCT/US16/18670 filed Feb. 19, 2016;
U.S. Prov. Ser. No. 62/647,454 filed Mar. 23, 2018;
U.S. Prov. Ser. No. 62/634,854 filed Feb. 24, 2018;
U.S. Prov. Ser. No. 62/587,038 filed Nov. 16, 2017;
U.S. Prov. Ser. No. 62/551,264 filed Aug. 29, 2017;
U.S. Prov. Ser. No. 62/452,883 filed Jan. 31, 2017;
U.S. Prov. Ser. No. 62/449,257 filed Jan. 23, 2017;
U.S. Prov. Ser. No. 62/443,769 filed Jan. 8, 2017;
U.S. Prov. Ser. No. 62/416,403 filed Nov. 2, 2016;
U.S. Prov. Ser. No. 62/405,930 filed Oct. 9, 2016;
U.S. Prov. Ser. No. 62/375,814 filed Aug. 16, 2016;
U.S. Prov. Ser. No. 62/362,643 filed Jul. 15, 2016;
U.S. Prov. Ser. No. 62/339,810 filed May 21, 2016;
U.S. Prov. Ser. No. 62/299,453 filed Feb. 24, 2016
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

FIELD

This patent specification generally relates to a medical device for use in tissue examinations and endoscopic surgery such as in urology and gynecology. More particularly, some embodiments relate to a portable, handheld, low-cost surgical endoscope device having a single-use portion and a multiple-use portion.

BACKGROUND

Conventional endoscopy, or direct vision used to examine the interior of a hollow organ or cavity of the body, uses a complex lens system for transmitting the image from the distal tip of the endoscope to a viewer. The lens system is typically a relay lens system in the case of rigid endoscopes or a bundle of fiber optics or an objective lens system in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

Disposable endoscopy is an emerging category of endoscopic instruments. In some cases the manufacture of endoscopes can be made inexpensive enough to be used on a single patient only. Disposable or single-use endoscopy lessens the risk of cross-contamination and hospital acquired diseases. Partially disposable endoscopy systems are discussed in U.S. Pat. Nos. 9,895,048, 9,895,848,10,278,563, and 10,292,571.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, an endoscope comprises: (a) a single-use portion that includes: (i) an insert housing that has a distal end and a proximal end and has a proximal port at said proximal end; (ii) a cannula that extends distally from the distal end of the insert housing, is configured for rotation about said longitudinal axis relative to said insert housing, and has a distal port at a distal portion of the cannula; (iii) an essentially straight lumen extending along said longitudinal axis, from said proximal port at the proximal end of the insert housing to the distal port at the distal portion of the cannula; (iv) an imaging and illumination module at said distal portion of the cannula; and a proximally facing electrical connector that is affixed to said insert housing and is operatively coupled with said imaging and illumination module; and (b) a multiple-use portion that includes: (i) a handle that has a distally facing electrical connector and a slot extending from a distal to a proximal portion of the handle; (ii) wherein said slot is open in a direction transverse to said longitudinal axis, said insert housing and said slot are shaped and dimensioned for the insert housing to snap in said slot in a motion transverse to said longitudinal axis and in a motion along said longitudinal axis to thereby secure the insert housing and the handle to each other and to electrically mate said electrical connectors; and (iii) a display module mounted on said handle and coupled with said imaging and illumination module through said electrical connectors.

The endoscope may include one or more of the following additional features: (a) the proximal port can protrude proximally from said handle; (b) one of said slot in the handle and said insert housing can comprise one or more ridges and the other comprises one or more grooves, wherein said grooves and ridges extend proximally and said ridges fit in said grooves and thereby facilitate securely holding the single-use portion in the multiple-use portion when the insert housing is snapped into the handle slot; (c) said one or more grooves and one or more ridges can extend to proximal ends of said insert housing and handle; (d) the handle can include a WiFi circuit configured to wirelessly transmit images taken with said imaging and illumination module; (e) said proximally facing electrical connector can be configured for coupling to external equipment comprising one or more of a workstation and image archiving and/or transmitting units, for sending thereto images taken with said imaging and illumination module; (f) said display module can be mounted on said handle for selective tilting and/or rotation relative to the handle about one or more axes; (g) said proximal port can be vertically in line with a center of said display module and less than 15 cm from a center of the display module, thereby placing the proximal port in a line and angle of sight of a viewer that includes both the display module and the proximal port; (h) said handle can have a top surface and two side surfaces and said slot in in one of the side surfaces of the handle.

According to some embodiments, a single-use, disposable portion of an endoscope comprises: (a) an insert housing that is elongated along a longitudinal axis and has an electrical connector fixedly mounted thereon; (b) a cannula extending distally from said insert housing along said axis; (c) wherein said insert housing is configured to releasably snap into and release from an elongated slot of a reusable handle that is open in a direction transverse to said axis; (d) wherein said cannula is mounted to said insert housing for rotation about said axis relative to said insert housing; (e) a lumen that extends along said axis, from a proximal port that starts at a location that is proximal from a proximal end of the insert housing and ends at a distal portion of the cannula; (f) an imaging and illumination module that is at the distal portion of the cannula and is operatively coupled to said electrical connector; and (g) a cable electrically coupling said imaging and illumination module with said electrical connector; (h) wherein said cable is inside said cannula and insert housing and is operatively coupled with said electrical connector and is sufficiently long and flexible to enable rotation of the cannula relative to the insert housing about said longitudinal axis over at least 180 degrees.

The endoscope described in the immediately preceding paragraphs can include one or more the following additional features: (a) said electrical contact can face proximally; and (b) said electrical contact can be affixed to said insert housing.

According to some embodiments, an endoscopic apparatus comprises: (a) a multiple-use handle with a pistol grip configured for grasping with a user's hand; (b) a slot in said handle, wherein said slot is above the pistol grip and extends along a longitudinal axis; (c) wherein said slot is open in a direction transverse to said longitudinal axis and is configured for removably snap-fitting therein an insert housing from which a cannula with an imaging module at a distal end thereof extends distally along said longitudinal axis; (d) a display module with a screen to display images, mounted to an upper portion of said handle for rotation and/or pivoting relative to the handle; and (e) image processing circuits inside the handle, operatively coupled with said display module when said insert housing is snapped into said slot and configured to display images sent thereto from said imaging module.

The endoscopic apparatus described in the immediately preceding paragraphs can include a lumen that extends essentially straight in said insert housing and cannula along said longitudinal axis and has a distal port extending proximally from a proximal end of the insert housing.

According to some embodiments, a method of imaging an internal site in a patient comprises: (a) providing a single-use portion that includes a cannula extending distally from an insert housing elongated along a longitudinal axis of the cannula; (b) providing a multiple-use portion that has a handle with a slot elongated along said longitudinal axis and open in a direction transverse to the longitudinal axis, said slot extending from a proximal end to a distal end of the handle, and a display module mounted on the handle to rotate and/or pivot relative to the handle about one or more axes; (c) snap-fitting said insert housing in said slot of the handle such that the housing extends from the proximal to the distal ends of the handle, by relative motion of the insert housing relative to the handle that includes motion in a direction transverse to the longitudinal axis; (d) electrically coupling an imaging module at a distal end of the cannula to electronic circuits in the handle that are electronically coupled to said display module; (e) said coupling comprising providing a cable between the imaging module and a first connector fixedly secured to the insert housing and providing a second connector fixedly mounted to the handle, wherein said relative motion of the insert housing and the handle automatically aligns the electrical connectors with each other and electrically couples said connectors to each other; (f) wherein said providing of the cable comprises providing a cable that runs inside the cannula and the insert housing to said first connector; (g) transmitting to said display module, over said cable and connectors and electronic circuits in the handle, images taken with said imaging module; and (h) selectively rotating the cannula relative to said insert housing and handle to direction of view of said imaging module.

The method described in the immediately preceding paragraphs can include one or more the following additional or more specific steps: (a) making the cable sufficiently long and flexible to enable rotation of the cannula relative to the housing and the handle of at least 180 degrees; (a) sealing said handle sufficiently to allow repeatedly sterilizing said handle in steam; (b) said providing said handle can comprise providing plural portions of an exterior wall of the handle and sealing them against each other using o-rings and/or gaskets to enable said sterilizing in steam; and (c) said providing of said single use portion and said reusable portion can further comprise providing a fluid port at a location proximal to both the handle and the insert housing and providing a lumen that extends along said longitudinal axis from said fluid port to a distal portion of said cannula.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 1 and 2 are right side and top views, respectively, of a portable endoscope having a disposable side-mountable portion, according to some embodiments;

FIGS. 8A and 8B are cross section and frontal view illustrating cannula rotation and other aspects of a portable endoscope having a side-mountable disposable portion, according to some embodiments;

DETAILED DESCRIPTION

Figure 3:
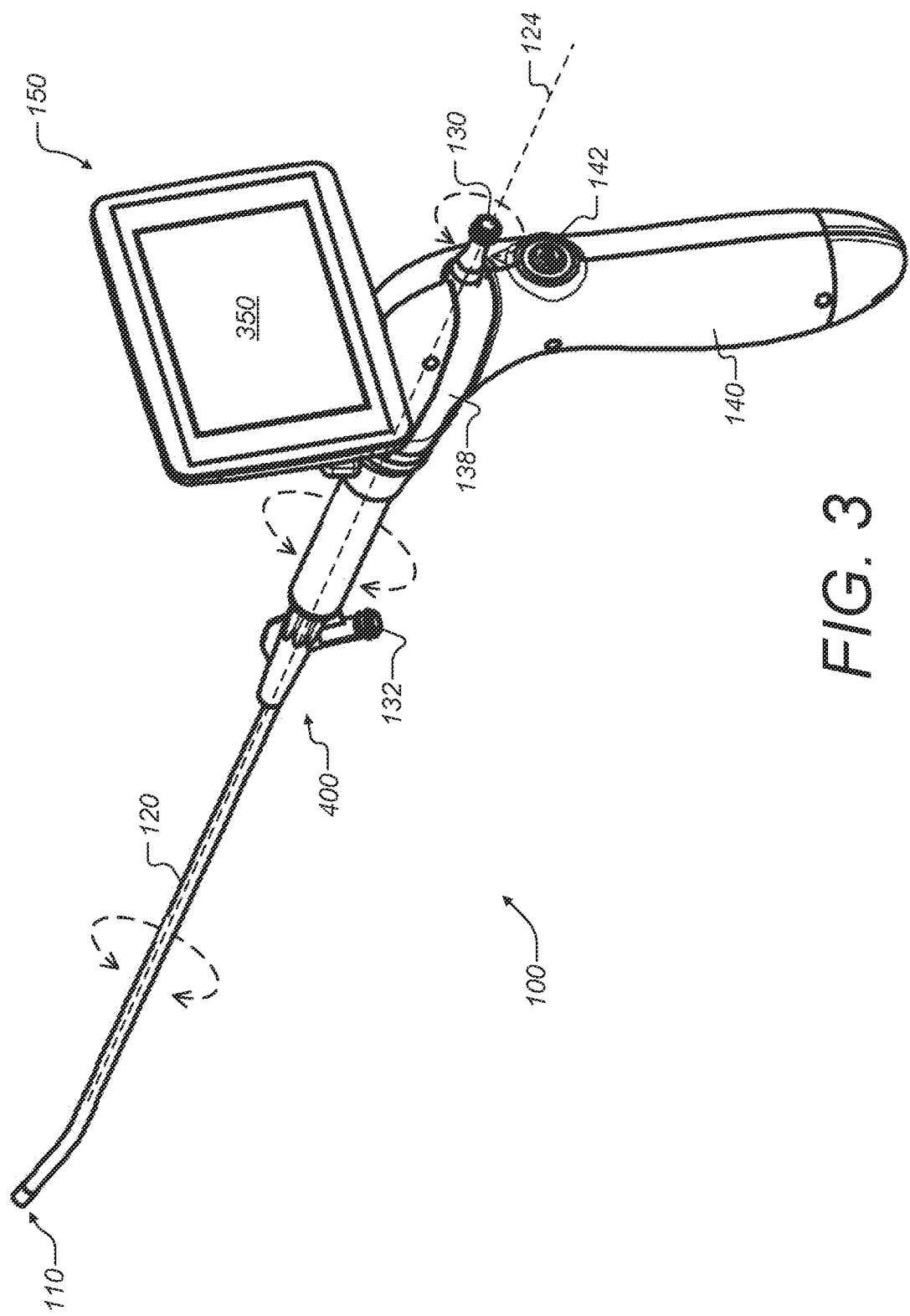
FIG. 3 is a perspective view of a portable endoscope having a disposable side-mountable portion, according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements. All patents and patent applications identified in this detailed description are hereby incorporated by reference in this patent specification.

FIGS. 1 and 2 are right side and top views, respectively, of a portable endoscope having a disposable portion, according to some embodiments. The portable endoscope 100 includes an elongated cannula 120 with a distal tip 110 for inserting into a hollow organ or cavity of the body. According to some embodiments, distal tip 110 is formed as a separate distal tip sub-assembly that is attached to the cannula 120. According to some embodiments, the distal tip 110 is about than 4.55 mm in diameter. For further details relating to a separate tip sub-assembly for a handheld endoscope, see: U.S. Pat. No. 9,895,048 (hereinafter referred to as "the '048 patent"); U.S. Ser. No. 15/462,331 filed Mar. 17, 2017 published as U.S. 2017-0188793 A1 (hereinafter the '331 application); and Int'l. Pat. App. No. PCT/US18/14880 filed Jan. 23, 2018 published as Int'l. Pub. No. WO/2018/136950 (hereinafter referred to as "the '880 application"). Distal tip 110 includes an imaging module and one or more LED light sources for viewing the organ or cavity into which tip 110 is inserted. The tip 110 also includes one or more fluid ports.

According to some embodiments, the cannula 120 is rigid, flexible or semi flexible and includes one or more fluid channels which are fluidly connected to port 132. Port 132 includes a Luer fitting to facilitate leak-free connection of port 132 with various medical fluid components (not shown). The one or more fluid channels or lumens in cannula 120 are also connected to one or more distal facing fluid ports of distal tip 110. According to some embodiments, one or more of the fluid channels or lumens in cannula 120 are also connected to proximal ports 130 and 430. Proximal ports 130 and 430 also include Luer fittings to facilitate leak-free connection with various medial fluid components (not shown). According to some embodiments, proximal port 130 is substantially in-line with the main longitudinal axis 124 of cannula 120 and thereby provides a substantially straight working channel through which rigid or semi rigid tools can pass through. According to some embodiments, only one proximal port 130 is provided and the second proximal port 430 is omitted. Providing a device channel that has straight proximal portion (through port 130), allows for improved ease in device insertion and manipulation. It has been found that providing the device port(s) (e.g. ports 130 and/or 430) in close proximity to the display module 150, and vertically in line with a center of display 150, provides significant ergonomic benefits. This placement makes it easier to insert a surgical instrument in port 130 or 430 and easier to manipulate the instrument because, to the user's eyes, the instrument is within the same sight and angle of the display screen. In particular, a short distance between the ports and display screen allows the operator to confine his/her range of vision to a relatively small area. According to some embodiments, the distance d between the proximal port (in this case port 130) and the center of the screen 350 of display module 150 is less than about 15 cm. According to some embodiments, the distance d is less than about 12 cm. According to some embodiments, the distance d is less than about 10 cm.

According to some embodiments, all three ports 130, 132 and 430 are connected to the same lumen or channel within cannula 120 and according to other embodiments, the ports are connected to two or more separate lumens. In the case where two or more ports are connected to a single lumen in cannula 120, one or more "duck bill" or similar valves can be used to prevent back flow or leak. According to some embodiments, wires running from the LED light sources and camera module in tip assembly 110 pass through a separate channel in cannula 120 to electrical connector 136 that is in addition to the one or more fluid channels. Electrical connector 136 is configured to form a releasable electrical connection with handle electrical connector 144 on the handle portion 140. Proximal to the fluid port 132 are a housing 134 and insert housing 138. According to some embodiments, the insert housing 138 is configured to slidably mate with, e.g., snap-fit in, a side-slot formed in handle 140 (see side-slot or socket 440 in FIG. 4A).

The endoscope 100 includes a handle portion 140 that is sized and shaped in a pistol-like fashion for easy grasping in a pistol-like grip by the endoscope operator (e.g. doctor or other medical professional). A display module 150 is rotatably and/or pivotally mounted on handle 140 via a bearing which can be a plain bearing made of plastic, and a rubber coated hinge. Also visible on handle 140 is image capture button 142. According to some embodiments handle 140 and display module 150 are configured to be re-usable and make up reusable portion 402 (shown in FIGS. 4A and 4B). According to some embodiments, one or more electronics modules 146 are included in handle 140, including electronics configured to provide one more of the following: camera control, video capture, video processing, video/data storage, battery charging and control, touch-screen processing, and WiFi communication. According to some embodiments, the electronics modules 146 include an electronic imaging system that supports automated features such as exposure control (AEC), gain control (AGC) and white balance (AWB). In addition, the electronics modules 146 are configured to provide ALC (auto light control) which controls the illumination of the object to be imaged. The camera and illumination modules in distal tip 110 and the imaging and control in electronics modules 146 are together configured as a "well-tuned" imaging system that provides a useful "Auto Mode." According to some embodiments, handle 140 is similar to handle 140 shown and described in the '048 patent, the '331 application, and the '880 application in that all are generally pistol-grip handles and may contain electronics and are coupled with displays, but handle 140 in the subject application differs in significant ways, including in the way it releasable couples and interacts with disposable portion 400.

FIG. 3 is a perspective view of a portable endoscope having a disposable side-mountable portion, according to some embodiments. The version of endoscope 100 shown includes only a single proximal port 130. According to some embodiments, different versions of the disposable single-use portion 400 can be made available to users depending upon their particular needs. Some examples are disposable portions in which an injection needle can protrude from the cannula tip, in a manner similar to that described in U.S. Pat. No. 10,278,563, or disposable portions with cannulas that have bendable distal ends, for example as described in U.S. patent application Ser. No. 16/447,251 filed Jun. 20, 2019, or disposable portions with cannulas that include a working channel through which surgical tools can pass, for example as in US 2019/0282071 A1, or disposable portions with cannulas that have distal ends shaped to scrape or otherwise take samples of tissue, for example as in U.S. Pat. No. 8,460,182. As shown by the dashed arrows, according to some embodiments the cannula 120 is rotatable about its longitudinal axis 124.

Figure 4A:
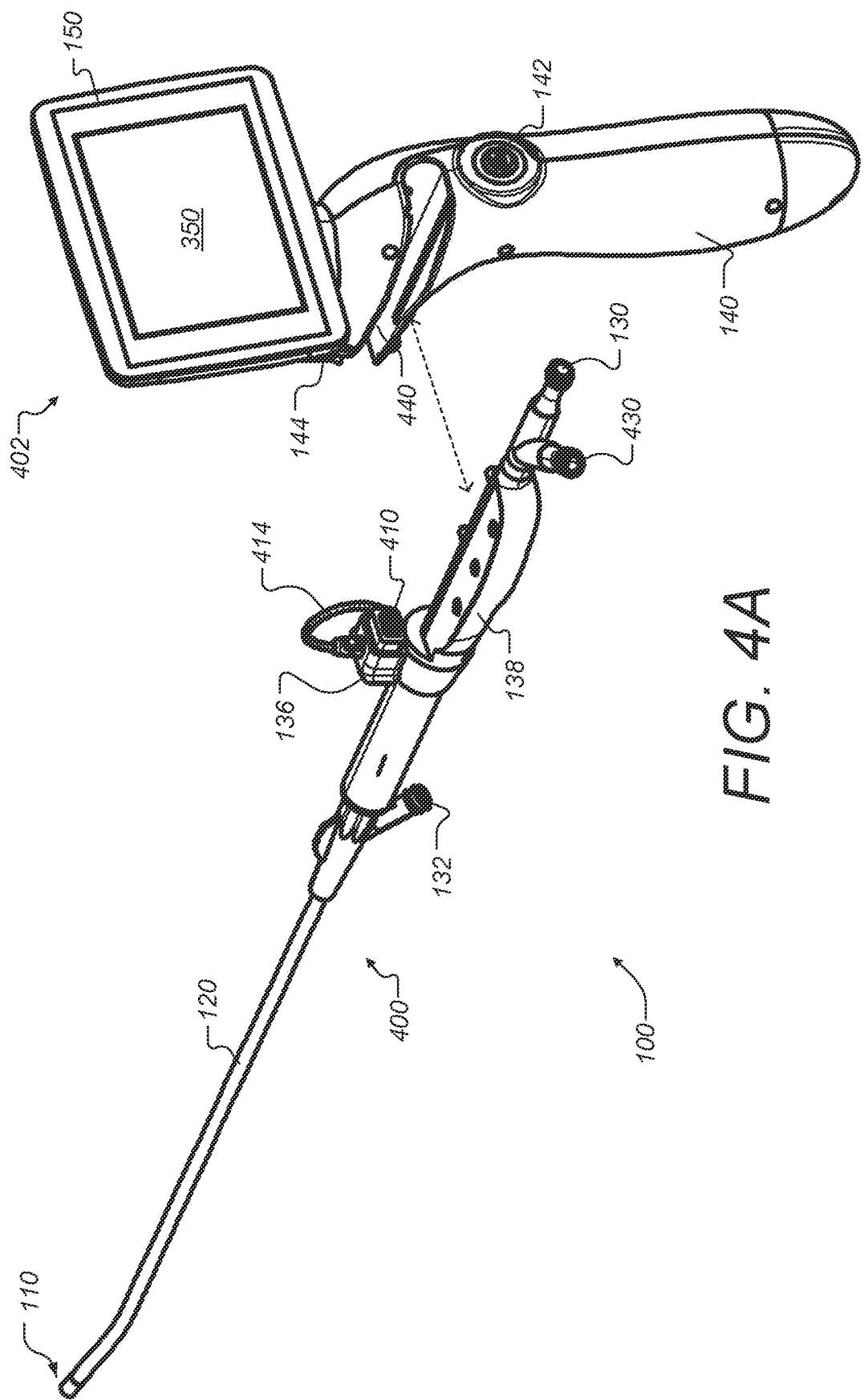
FIGS. 4A and 4B are perspective views illustrating further aspects of a portable endoscope having a side-mountable disposable portion, according to some embodiments.
Figure 4B:
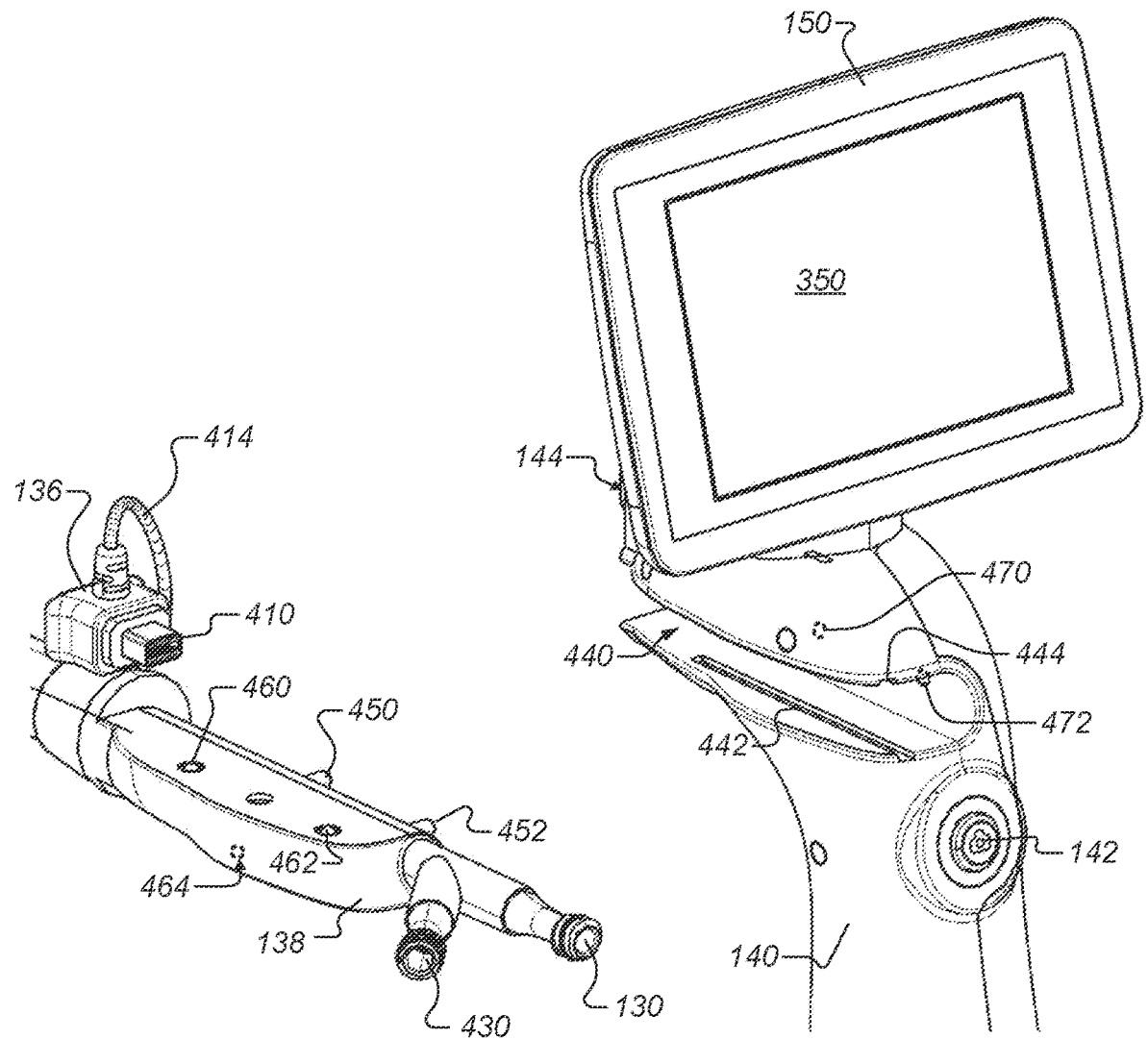

FIGS. 4A and 4B are perspective views illustrating further aspects of a portable endoscope having a side-mountable disposable portion, according to some embodiments. Illustrated more clearly in FIG. 4A are the single-use disposable portion 400 and the multi-use reusable portion 402 of endoscope 100. Single use portion 400 includes cannula 120, distal tip 110, electrical connector 136, ports 130, 132 and 430, and insert housing 138. The reusable portion 402 includes the handle 140 and display module 150. As shown by the dashed arrow, the single use portion 400 slides or snaps into the side of the reusable portion 402, by motion in a direction transverse to longitudinal axis 124. In particular, the insert housing 138 of single use portion 400 is dimensioned to fit snugly but releasably into the side slot 440 formed in handle 140 of reusable portion 402. The mating of insert housing 138 into slot 440 is configured to provide a secure physical connection between single use portion 400 and reusable portion 402. The electrical connections between the two portions 400 and 402 are made using electrical connector 136 and handle electrical connector 144. Separating the physical connections from electrical connections has been found to provide advantages including greater resistance to fluid contamination to the electrical components and easier and more intuitive mating of the disposable and reusable portions. In addition, this type of electrical connection enables the alternative of conveniently connecting the disposable portion 400 to an electronic unit other than handle 140, such as a tower that contains computing equipment and a display or some other image processing and/or image storage equipment or equipment for transmitting images from portion 402 to remote locations such as hospital workstations or remote medicine facilities. According to some embodiments, the electrical connector 136 is connected to the body of single use portion 400 via a flexible cable 414, and is configured to allow for rotation of the cannula as shown in the dashed arrows of FIG. 3. A distal portion of cable 414 is inside cannula 120 but a proximal portion is outside, exposed to the environment, and is sufficiently long and flexible to enable rotation of cannula 120 relative to housing 134 and handle 140.

FIG. 4B shows further details of the physical and electrical connections between the single use portion and reusable portion of portable endoscope 100. According to some embodiments, the electrical connectors 136 and 144 use a standard electrical connection scheme such as mini-display port (type DP20), which is also used for versions 1 and 2 of Thunderbolt connectors. In FIG. 4B a male connector 410 is shown that can mate with a female connector 144 on handle 140. For the mechanical connection, the insert housing 138 can include positioning aids such as positioning balls 460, 462 and 464 which are spring-loaded and can engage with grooves 442 and 444 formed within slot 440. Additionally, posts 450 and 452 are formed on insert housing 138 and mate with holes 470 and 472 on the inside of slot 440 of handle 140.

Figure 5:
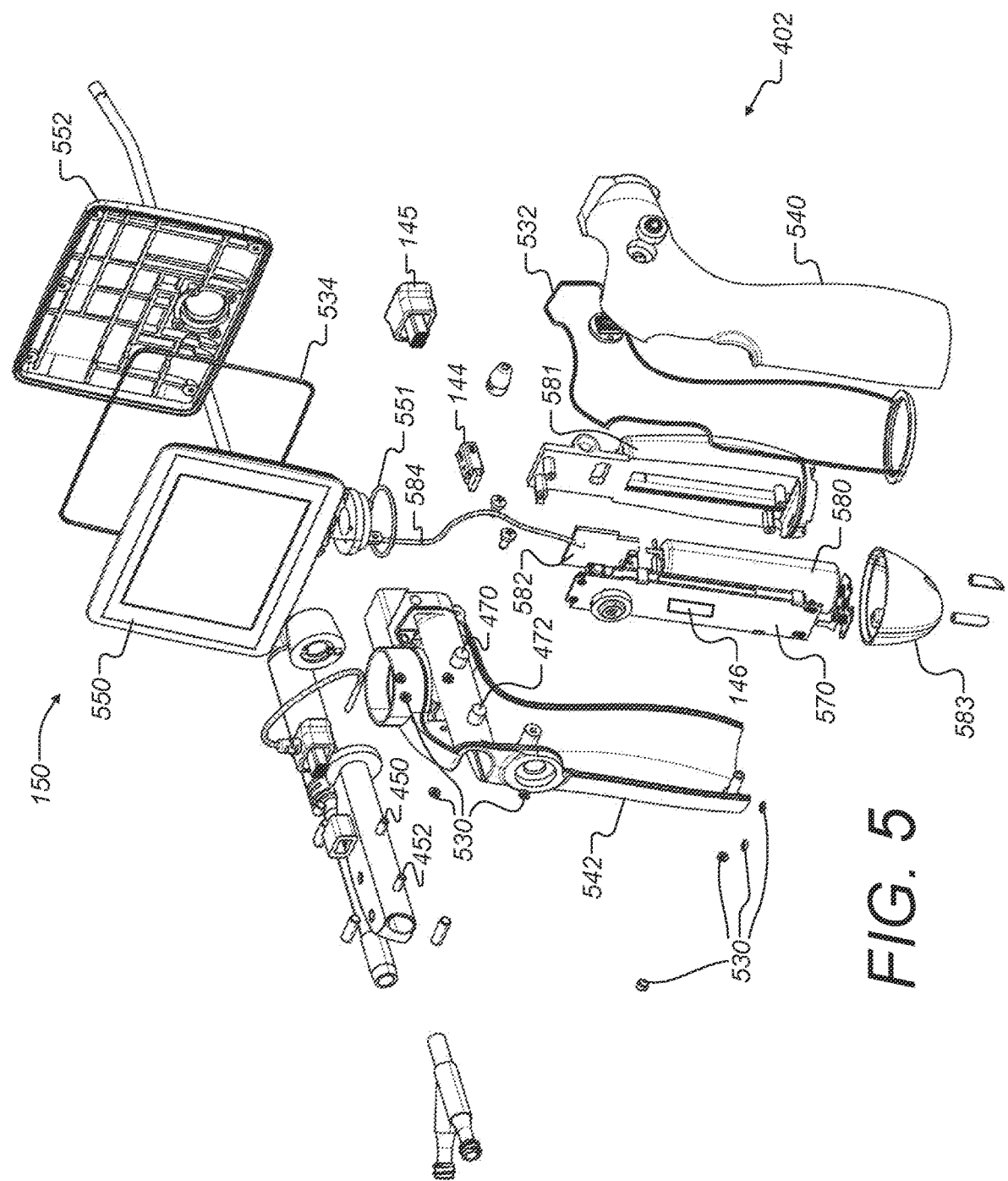
FIG. 5 is an exploded perspective illustrating sealing and other aspects of a portable endoscope having a side-mountable disposable portion and a fluid-resistant handle portion, according to some embodiments.

FIG. 5 is an exploded perspective view illustrating sealing and other aspects of a portable endoscope having a side-mountable disposable portion and a fluid-resistant handle portion, according to some embodiments. Many of the components of the reusable portion 402 are sealed using o-rings and/or gaskets, including left and right handle cover pieces 542 and 540, respectively, which are sealed to each other using an o-ring or gasket 532. Similarly, the front cover 550 and rear cover 552 of the display module 150 is sealed using an o-ring 534. The display module 150 are sealed to the left handle cover piece 542 using o-ring 551. Various other openings are sealed with o-rings such as o-rings 530. Front cover 581 and bottom cover or piece 583 similarly may be sealed against right and left handle cover pieces 540 and 542 by o-rings and/or gaskets.

Also shown in FIG. 5 is the main printed circuit board 570 on which electronics modules 146 are mounted. Rechargeable lithium ion battery 580 is used to power the electronics, display module 150, and also the camera module and LEDs on the distal tip through electrical connector 144. According to some embodiments, Wi-Fi functionality is included, and shown in FIG. 5 are WiFi board 582 and WiFi antenna 584.

Figure 6:
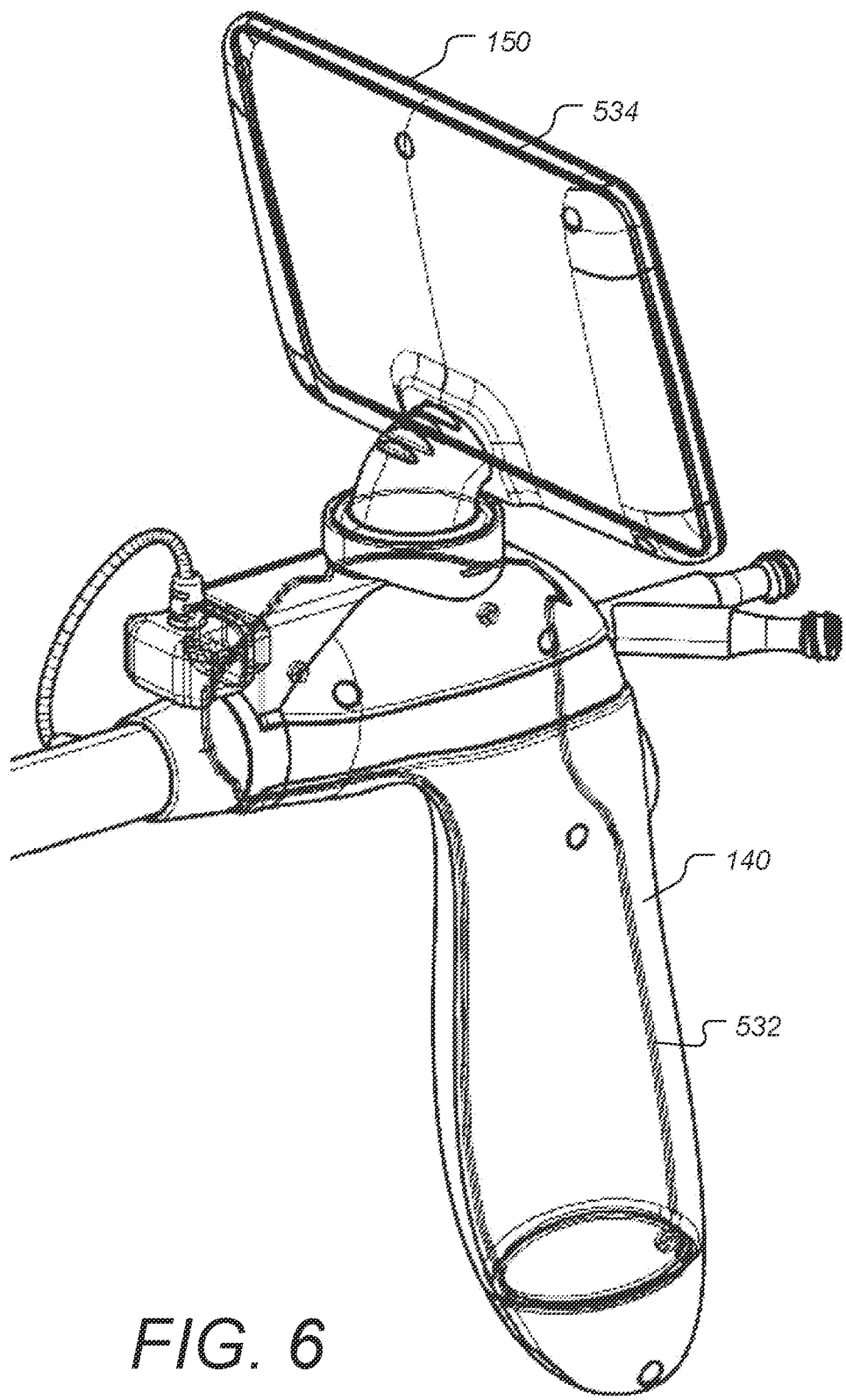
FIG. 6 is a perspective view illustrating sealing and other aspects of a portable endoscope having a side-mountable disposable portion, according to some embodiments.

FIG. 6 is a perspective view illustrating sealing and other aspects of a portable endoscope having a side-mountable disposable portion, according to some embodiments. The o-ring seals 532 and 534 are shown in this view. The o-ring seals shown and described in FIGS. 5 and 6 enable the reusable portion 402 of the portable endoscope to be highly water resistant. For example, handle 140 can be configured to comply with the IXP 7 standard and can withstand being submerged for up to 30 minutes 0.15 meters to 1 meter below a fluid surface. Following use, endoscope components that will be re-used can be disinfected and/or sterilized prior to re-use to prevent cross contamination. According to some embodiments, providing the sealing as shown and described provides a level of fluid-resistance for the reusable portion 402 to be soaked in fluid such as an alcohol, for cleaning, disinfection and/or sterilization. According to some embodiments, with the addition of a removable silicone plug 145 to seal the electrical connector 144, reusable portion 402 can be sterilized by submersion in EO (Ethylene oxide). According to some other embodiments, the reusable portion 402 is constructed such that it can withstand repeated autoclave such as hot steam at 134° C.

Figure 7:
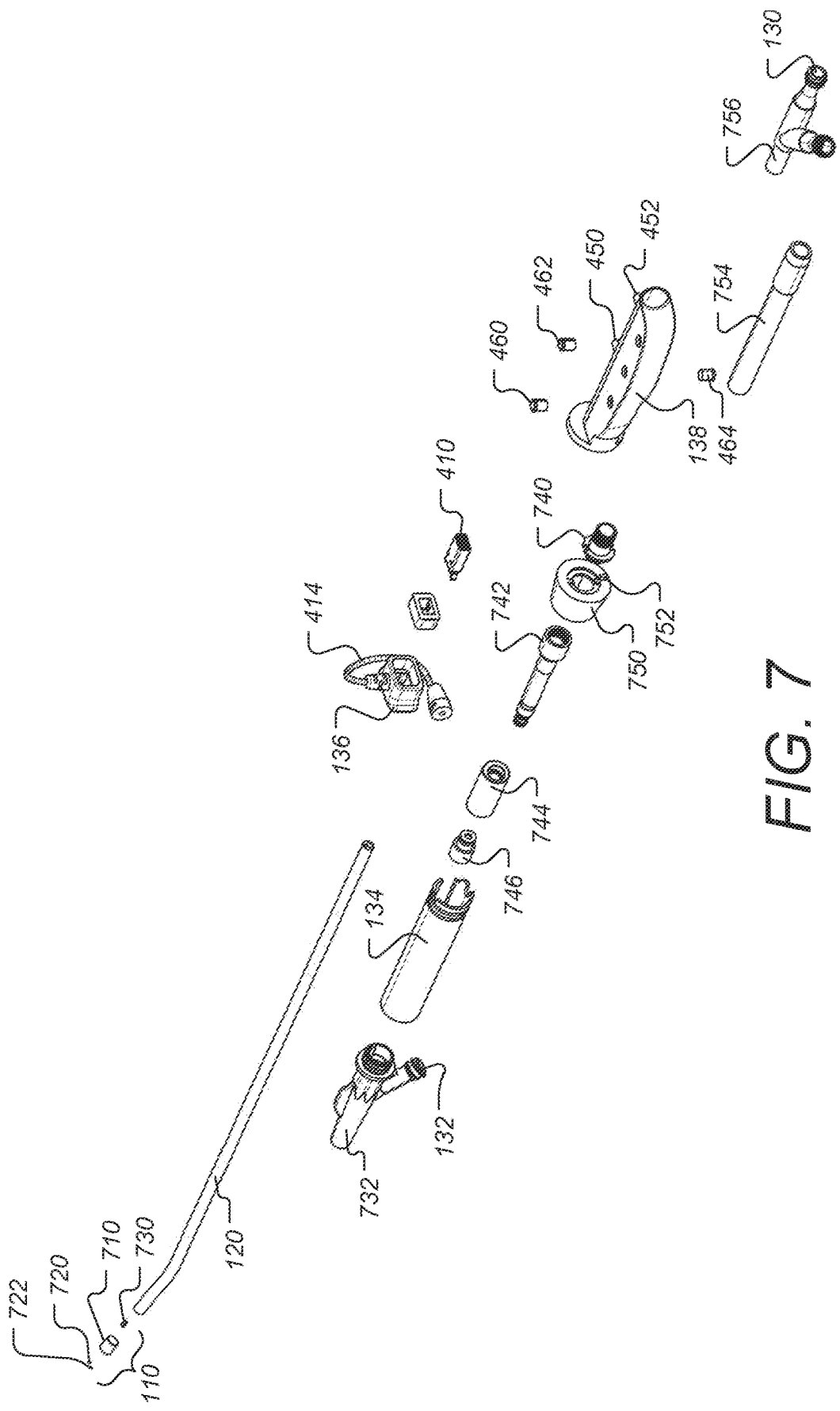
FIG. 7 is an exploded perspective illustrating cannula rotation and other aspects of a portable endoscope having a side-mountable disposable portion, according to some embodiments.

FIG. 7 is an exploded perspective illustrating cannula rotation and other aspects of a portable endoscope having a side-mountable disposable portion, according to some embodiments. At the distal end, distal tip 110 is shown to include tip housing 710, two or more LEDs of which only LEDs 720 and 722 are shown as an example, and camera module 730. The proximal end of cannula 120 is inserted into the distal end of fluid hub body 732. Hub body 732 is fixed at its proximal end to housing 134, which in turn is fixed at its proximal end to base 750. Within housing 134 is insert tube connector 746 that is shaped at its distal end to accept the proximal end of cannula 120. Connector 746 is connected at its proximal end to connector piece 744 which can be attached to connector 746 by screw threads and/or epoxy. The connector piece 744 is attached to joint-working channel piece 742. The base 750 is held in place by being "sandwiched" between flanges on the proximal end of channel piece 742 and on connector piece 740. Piece 740 is attached to tube 754. The proximal end of tube 754 is fixed to luer port piece 756. Tube 754 is configured to rotate freely within insert housing 138. The insert housing 138 and electrical connector 136 remain stationary relative to the handle 140, while most of the other components rotate about axis 124. In particular, according to some embodiments, the following components rotate together about axis 124 as a single unit: distal tip 110, canula 120, hub 732, housing 134 connectors 746 and 744, joint-working channel piece 742, base 750, connector piece 740, tube 744, and luer piece 756. According to some embodiments, the rotation of the cannula 120 and other components is limited to slightly less than 360 degrees (e.g. 350 degrees such as shown in FIG. 8B, or at least 180 degrees) so that flexible cable 414 does not become overly strained due to excessive rotation. The base 750 can include a tab 752 that fits into a circular slot 810 formed in on the distal face of the flange of insert housing 138 (shown in FIG. 8A)

FIGS. 8A and 8B are cross section and frontal view illustrating cannula rotation and other aspects of a portable endoscope having a side-mountable disposable portion, according to some embodiments. According to some embodiments, slot 810 is shaped to limit the rotation of the cannula 120 and other components by limiting the movement of tab 752 (shown in FIG. 7) of base 750. Note that the working channel in the cannula may be slightly off center or off axis 124 due to the cannula containing multiple lumens. The connector piece 744 can be shaped to bring the working channel more towards the central longitudinal axis 124.

Figure 9:
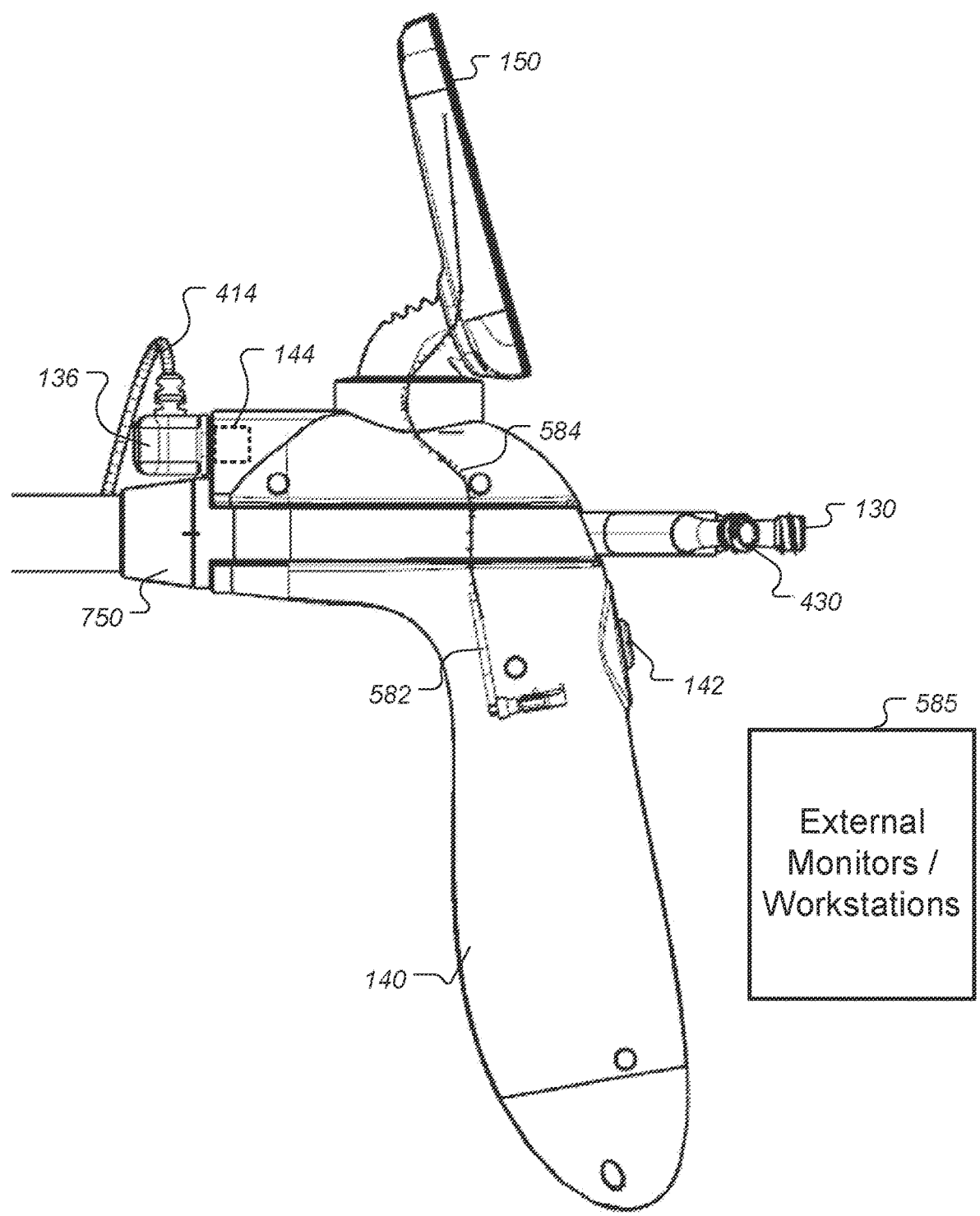
FIG. 9 is a side view illustrating a WiFi antenna arrangement and other aspects of a portable endoscope having a side-mountable disposable portion, according to some embodiments.

FIG. 9 is a side view illustrating a WiFi antenna arrangement and other aspects of a portable endoscope having a side-mountable disposable portion, according to some embodiments. WiFi board 582 and the location of WiFi antenna 584 is shown. Note that WiFi antenna 584 can extend to and along the back of the touch screen of display module 150 to reduce the effects of screening by metal portions of handle 140. According to some embodiments, the WiFi module on board 582 and the antenna 584 can transmit video to WiFi receivers which can be used for other external monitors or to workstations 585, for example.

Figure 10:
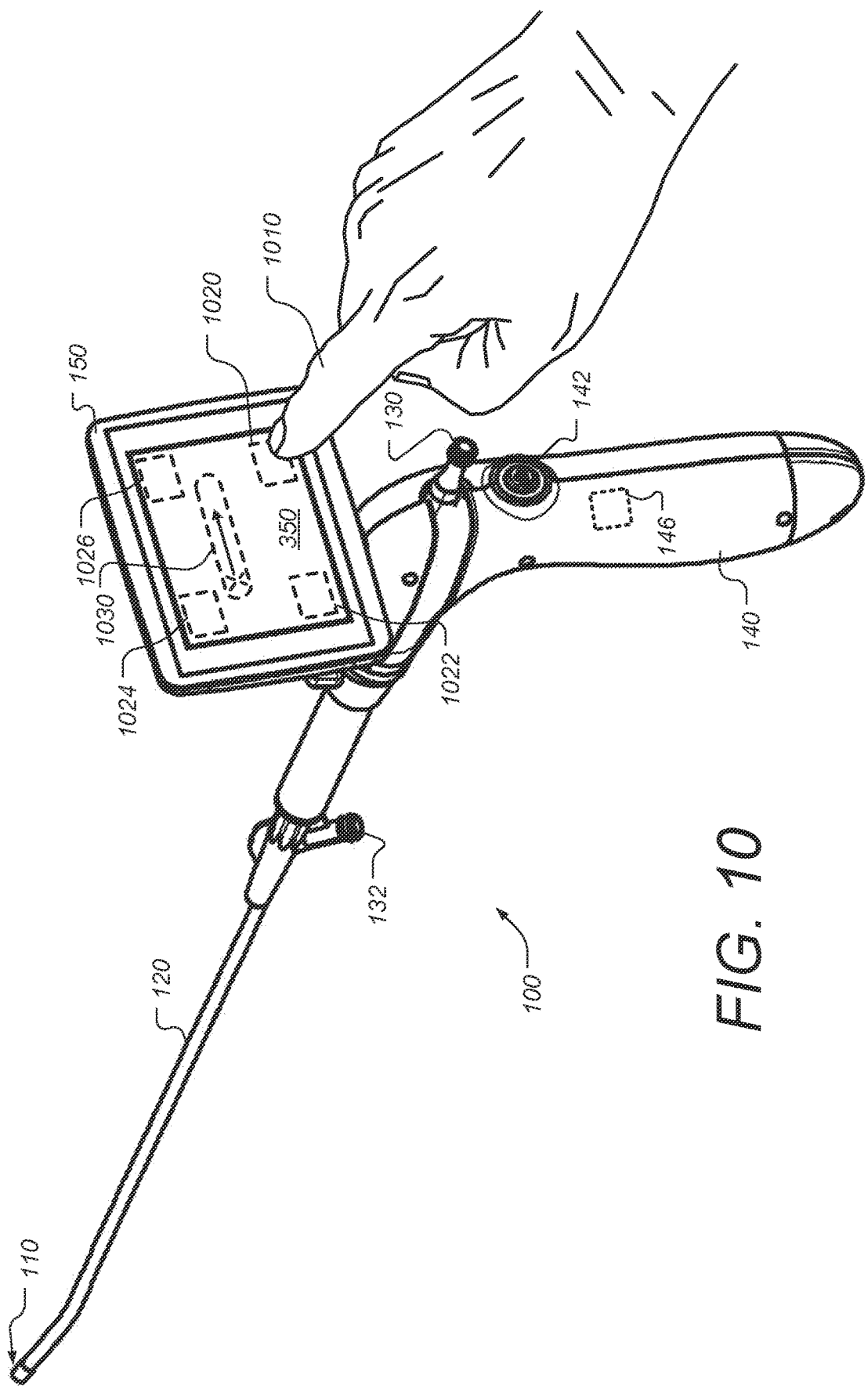
FIG. 10 is a perspective view illustrating aspects of a touch sensitive video display screen, according to some embodiments.

FIG. 10 is a perspective view illustrating aspects of a touch sensitive video display screen, according to some embodiments. As described supra, electronics modules 146 in handle 140 include an electronic imaging system that supports automated features such as exposure control (AEC), gain control (AGC) and white balance (AWB). In addition and integrated, is the ALC (auto light control) which controls the illumination of the object to be imaged. The camera and illumination modules in distal tip 110 and the imaging and control in electronics modules 146 are together configured as a "well-tuned" imaging system that provides a useful "Auto Mode." However, in certain cases, especially in endoscopy, it is sometimes advantageous to use a "Manual Mode". In a handheld portable endoscope 100, when the distal tip 110 is inside a cavity, Auto Mode works well in most situations. But in certain situations, for example when the camera on distal tip 110 is proximal to a wall that is tangential with the direction of the view of the camera module, part of the image field (the wall due to its proximity to the illuminating LEDs) is very bright compared to other areas which are further away from the LEDs. In order to better visualize the wall (or the portion that is close up to the camera tip), a "Manual Mode" can be used in which all the automated imaging functions are turned off. In FIG. 10, a toggle button such as one of the corner location buttons 1020, 1022, 1024 and 1026 on the touch screen 350 can be used to toggle or switch between Auto Mode and Manual Mode. According to some other embodiments, a hardware button on the handle 140 can be used instead of or in addition to the touch screen button, to switch between the Auto Mode and Manual Mode. Furthermore, the "Manual Mode" can have 2 or 3 steps to reduce the LED brightness to facilitate the visualization of the surface of interest. Some aspects of such Auto Mode and Manual Mode are described in U.S. Pat. No. 10,292,571.

According to some embodiments, Auto Mode is configured to provide full automatic AGC, AEC and ALC, while Manual Mode turns off AGC, AEC and ALC, and sets the LED brightness at 50% (or some other predetermined level such as 75%) of its default brightness Screen 350 can be configured for non-contact or non-touch operation such that clinical operators need not remove their gloves in order to push and activate a button on the screen 150. According to some embodiments, buttons 1020, 1022, 1024 and 1026 are virtual touch buttons that are floating above the display screen 350. They can be located near the corners or edges of the screen as shown. User can use cross motion (sliding "X" or "+" shape) at location 1030 on the screen 350 to close and hide the floating buttons. User can use circular motion (not shown) to bring back up the floating buttons.

Figure 11A:
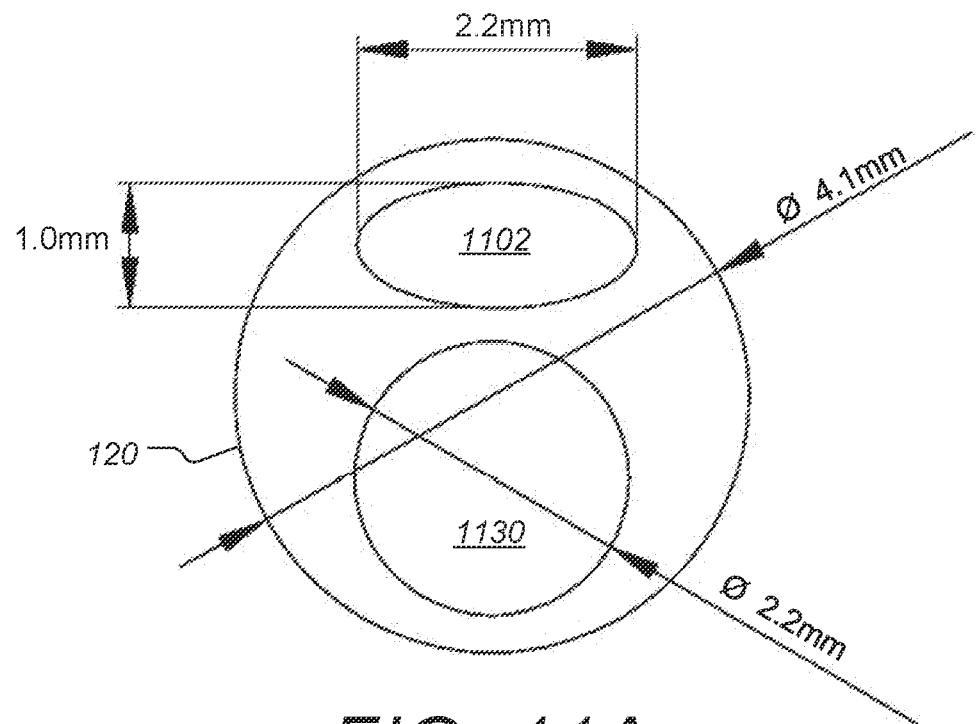
FIGS. 11A and 11B are cross sections showing further detail of a cannula and a distal tip that form part of a side-mountable disposable portion of a portable endoscope, according to some embodiments.
Figure 11B:
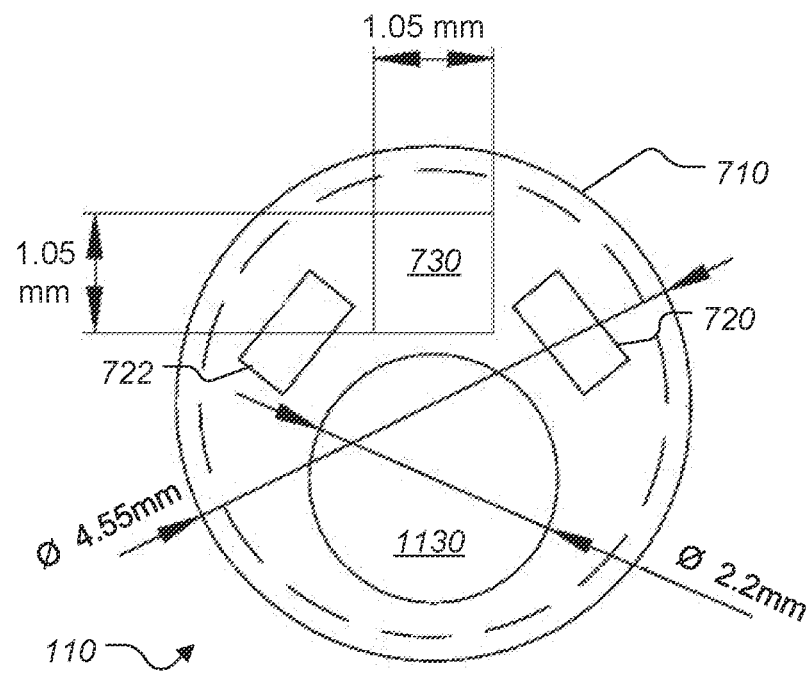

FIGS. 11A and 11B are cross sections showing further detail of a cannula and a distal tip that form part of a disposable portion of a portable endoscope, according to some embodiments. FIG. 11A shows some example dimensions for the cannula 120. Cannula 120 has an O.D. of 4.1 mm. The working channel lumen has an I.D. of 2.2. mm and the cable lumen 1102 is oval with dimensions shown. Cable lumen 1102 can be used to carry the electrical wires leading to the camera module and LEDs on distal tip 110. In FIG. 11B the dimensions and placement of camera module 730, LEDS 720 and 722 are shown. Camera module 730 can have a square area 1.05 mm per side, and each of LEDs 720 and 722 can be a rectangle with a larger side approximately the same length as a side of camera 730.

According to some embodiments, the endoscope 100 described herein can be used for gynecology applications. For example, an endometrial biopsy device, such as a Pipelle, an endometrial biopsy cannula such as the SoftFlex device offered by Integra Live Sciences Corp. of New Jersey, a device such as the EndoSampler device offered by MedGyn in Illinois, or a surgical curette, etc. can be inserted through the working channel for endometrial biopsy.

Figure 12:
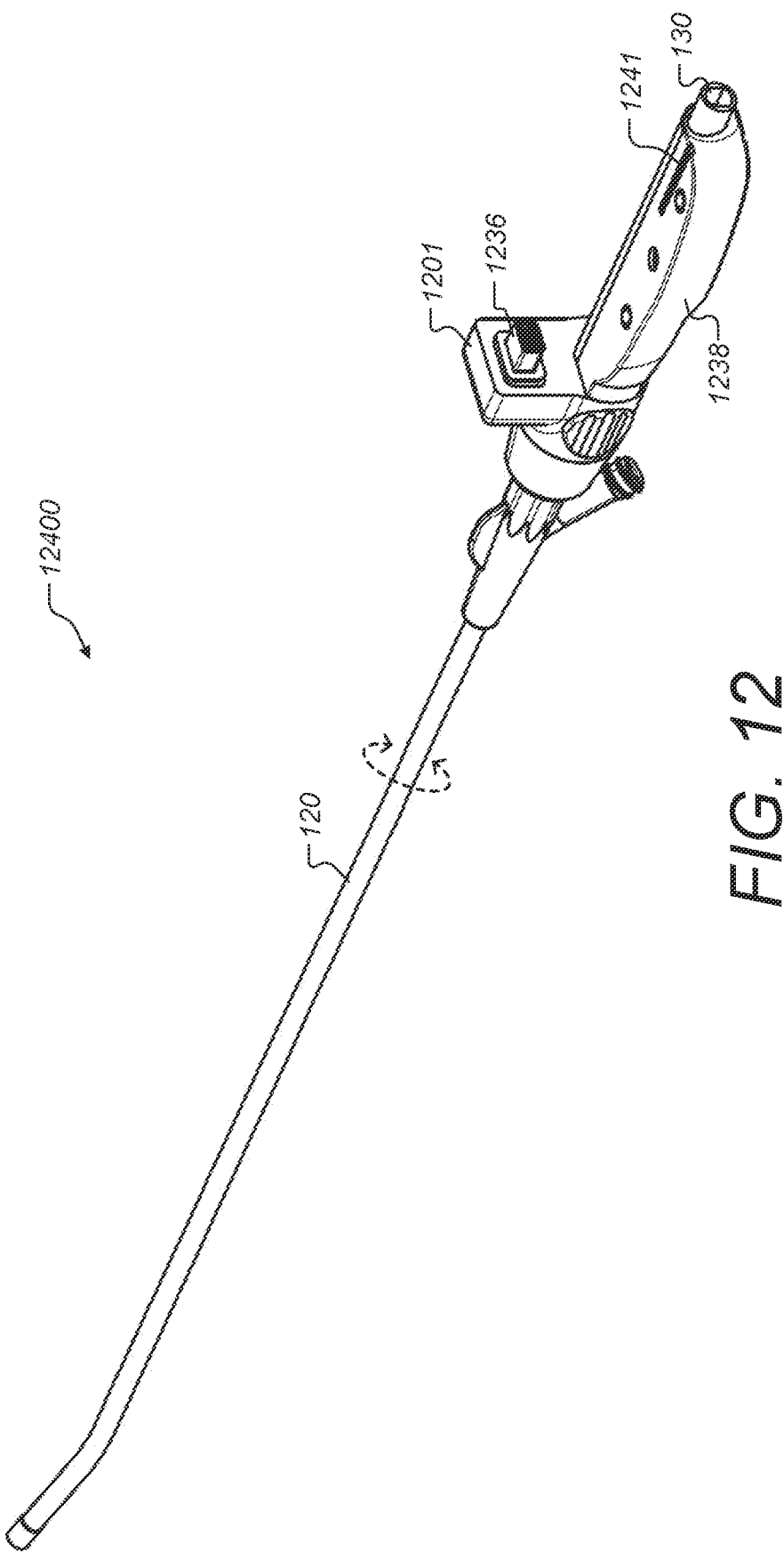
FIG. 12 is a perspective view illustrating a single-use portion of an endoscope, according to some embodiments.
Figure 13:
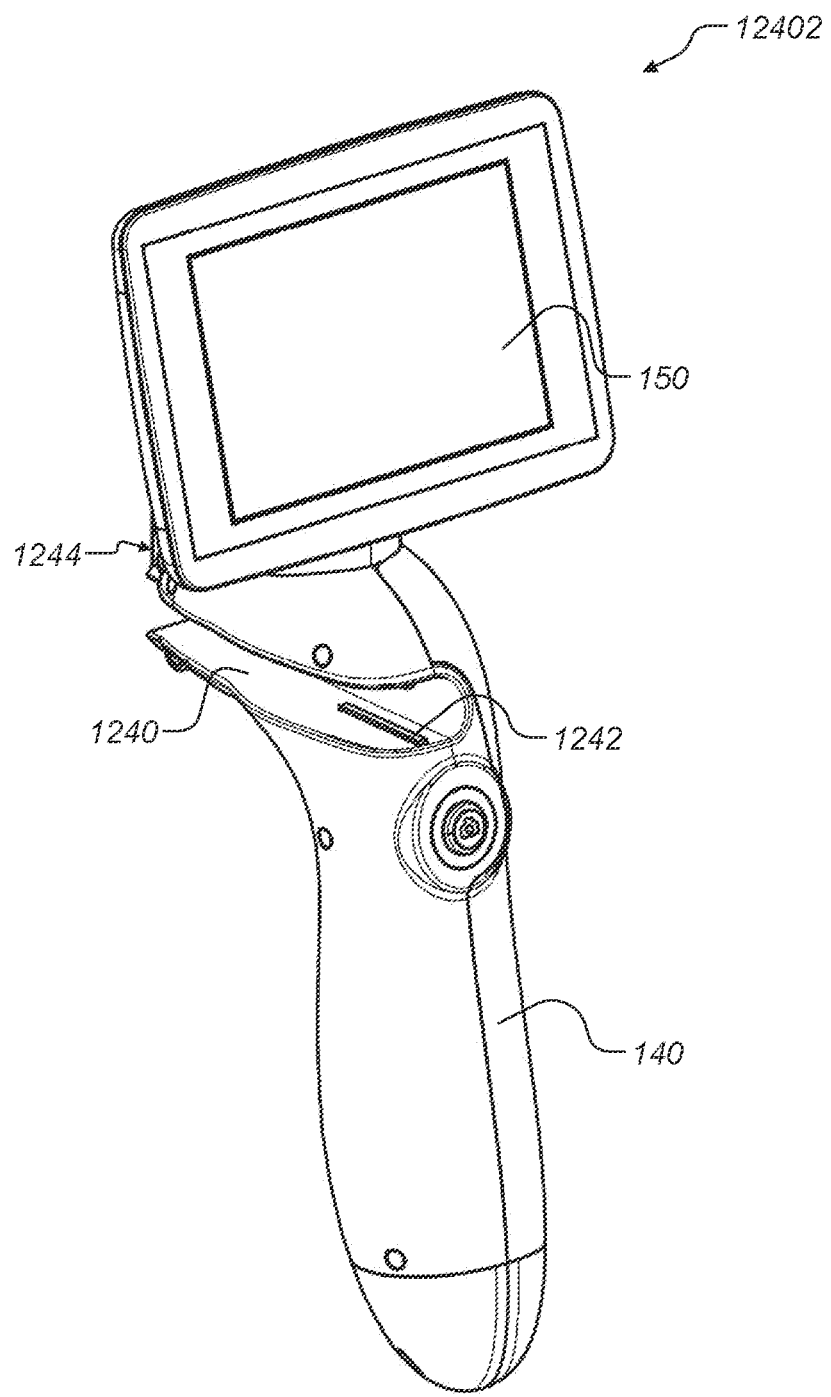
FIG. 13 is a perspective view illustrating a multiple-use portion of an endoscope, according to some embodiments.
Figure 14:
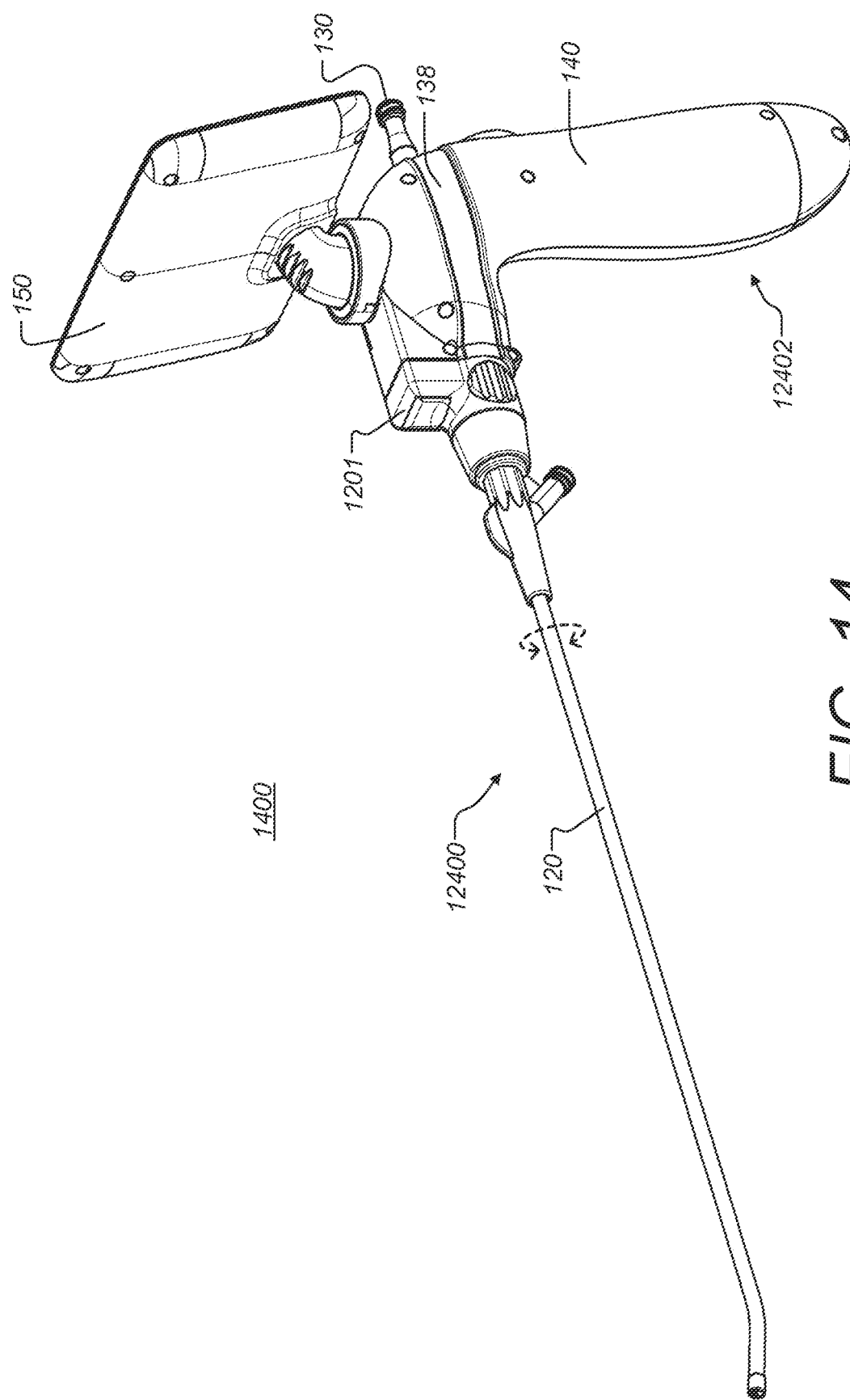
FIG. 14 is a perspective view of an endoscope assembled with the single-use portion and multiple-use portion shown in FIGS. 12 and 13, according to some embodiments.

FIGS. 12-14 illustrate an endoscope that has a different way of mating the single-use portion seen in FIG. 12 to the multiple-use portion seen in FIG. 13 into the endoscope seen in FIG. 14, according to some embodiments. The single-use portion 12400 shown in perspective in FIG. 12 can be otherwise like the single use portion 400 seen in FIG. 4A but has a different electrical connector 1236 affixed to an upwardly extending post 1201 affixed to insert housing 1238. Single-use portion 12400 preferably omits port 430 seen in FIG. 4A although such a port can be added if desired. This configuration replaces an electrical connector such as connector 136 seen in FIG. 4A. Insert housing 1238 can be otherwise like housing 138 in FIG. 4A but preferably further includes a ridge 1241 at its upper surface that extends proximally, preferably to the proximal end of the insert housing, and may further include a like ridge at its underside. Cannula 120 of FIG. 12 is rotatable about its longitudinal axis, as described in connection with FIG. 3, for example. The multiple use portion 12402 seen in FIG. 13 is otherwise like the multiple-use portion 402 of FIG. 4A but has a distally facing electrical connector 1244 in place of electrical connector 144 seen in FIG. 4A. In addition, multiple-use portion 12402 preferably includes a proximally extending groove 1242 at its bottom surface and may include a matching groove at its upper surface. FIG. 14 illustrates the single-use portion 12400 and the multiple-use portion 12402 assembled into endoscope 1400.

Assembling the single-use and multiple-use portions of FIGS. 12 and 13 into the endoscope of FIG. 14 is convenient, quick, and helps avoid assembly errors. Single-use portion 12400 typically comes sealed in a sterile pouch. The user removes it from the package and slides a proximal part of insert housing 138 into slot 1240, in the left-to-right direction as seen in FIGS. 12 and 13, preferably until ridges 1241 snap into grooves 1242. The user then snaps insert housing 138 in the proximal direction so electrical connector 1236 engages connector 1244 and the proximal face of post 1201 presses against the distal face of handle 140. The contact between post 1201 and the distal face of handle 140 should be sufficient to keep fluids from entering handle 140 or reaching connectors 1236 and 1244 but for extra security the distal face of handle 140 can be further provided with a peripheral seal that would be squeezed when post 1201 presses against handle 140. As in examples described above in this patent specification, display unit 150 is mounted on handle 140 for tilting relative to the handle about at least one axis, and cannula 120 is mounted for rotation about its longitudinal axis relative to insert housing 138 and handle 140.

Assembling the endoscope of FIG. 14 automatically aligns the two electrical connectors, 1236 and 1244. The action of snapping insert housing 138 into slot 1240 of handle 140 in a direction transverse to the longitudinal axis of cannula 120, automatically aligns connectors 1236 and 1244. Therefore, moving insert housing 138 proximally relative to handle 140 automatically correctly mates connectors 1236 and 1244 into electrical contact, without the user having to look if they are aligned.

According to some embodiments, slot 1240 can be at the side of handle 140 opposite the side seen in FIG. 13. Slot 140 alternatively can be at another portion of handle 140 such as closer to or at the top of handle 140, in which case display unit 150 can be mounted to allow insert housing 138 to reach slot 1240.

According to some embodiments, sing-use portion 12400 can be used for a medical procedure without handle 140 and display unit 150, by electrically coupling connector 1236 by cable or via a WiFi link to a device such as a workstation or a tower unit serving the functions of display unit 150. (See FIG. 9.) Single-use portion 400 seen in FIG. 4A can be likewise coupled to a devise such as a workstation or tower unit. Then, single-use unit 12400 or 400 can be held as a pencil or can be gripped at the user's preference. According to some embodiments, if single-use portion 12400 or 400 is to be used with an external display and processor, without handle 140 and display unit 150, a simplified handle can be provided that is otherwise like handle 140 but contains no electronics or minimal electronics for users who may prefer a pistol-grip handle. In that case, the distal end of the simplified handle may be shortened to allow cable access to connector 1238 but need not be shortened if WiFi communication is used.

Figure 15:
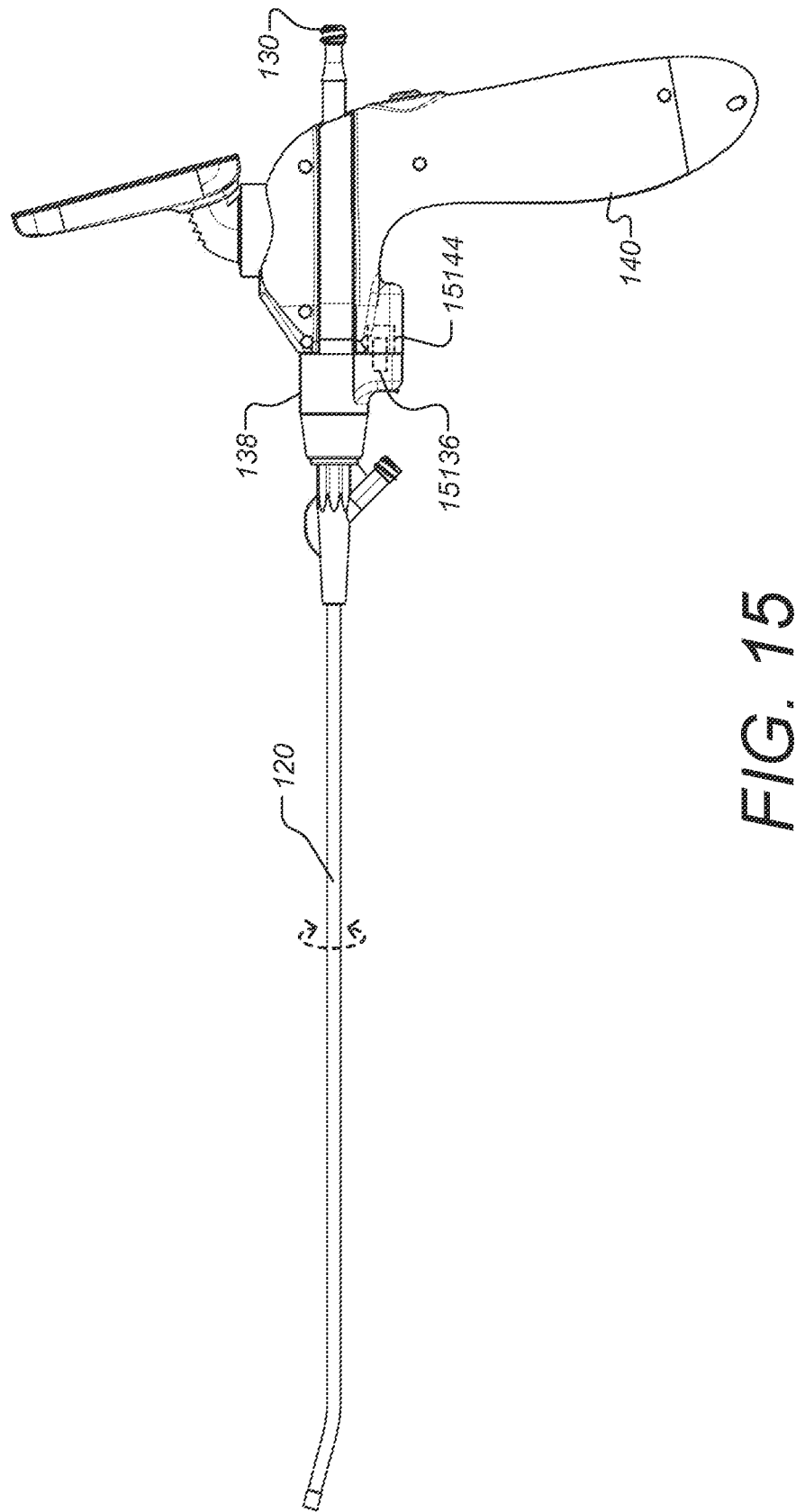
FIG. 15 is a perspective view of an endoscope like that of FIGS. 1 and 2 but with a different arrangement of electrical contacts, according to some embodiments.

FIG. 15 illustrates an endoscope according to some embodiments that is otherwise like the endoscope of FIGS. 1 and 2 but has its electrical connector 15136 mounted to mate with an electrical connector 15144 fixedly mounted to the underside of a distal portion of handle 140. In other respects, connector 15136 can be like connector 136 and extend from insert housing on a flexible cable like cable 414 in FIG. 4B, and in other respects connector 15144 can be like connector 144 in FIGS. 1 and 2.

Figure 16:
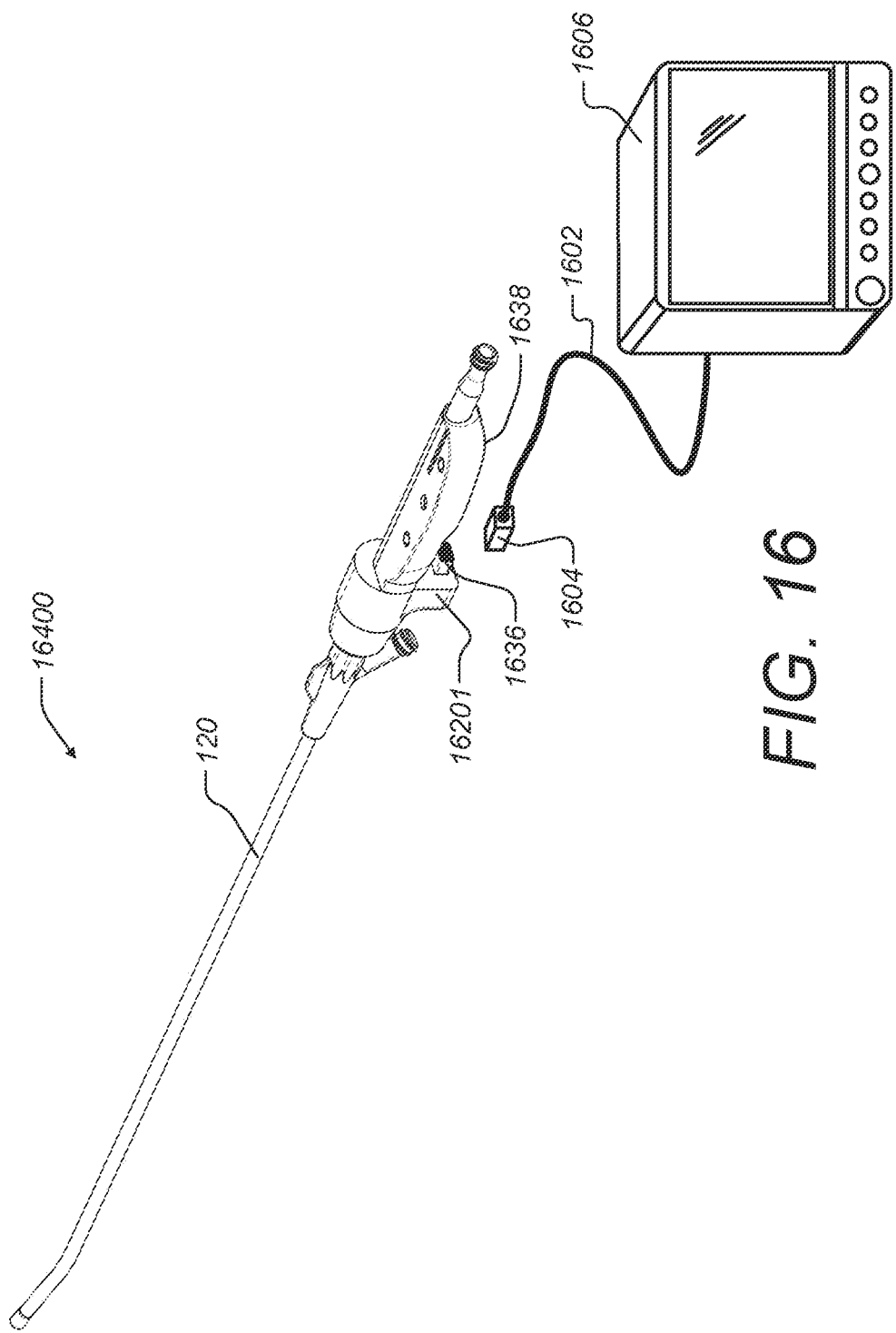
FIG. 16 is a perspective view of a single-use endoscope portion configured to interact with a remote image processor and display, according to some embodiments.

FIG. 16 illustrates in perspective a single-use endoscope portion configured to interact with a remote image processor and display. Single-use portion 16400 is like single-use portion 1400 of GIG. 12 but its electrical contact 1636 is on a post 16201 that extends down from insert housing 1638 while post 1201 in FIG. 12 extends up from insert housing 1238. A cable 1602 has a free end terminating in an electrical contact 1604 configured to mate with electrical contact 1636 for communication between the imaging and illumination module at the distal end of cannula 120 and a processing and display unit 1606 that is remote from single-use unit 16400 and is configured to perform the functions of the electronic circuits in handle 140 and the functions of display module 150 described for other embodiments above. One advantage of the configuration of FIG. 16 is that a user can hold single unit 16400 in different ways—for example can gasp insert housing 1638 as a stick or can hold single-use portion 16400 as pencil. Placing electrical connector 1636 below insert housing 1638 places cable 1602 below single-use portion 16400, which has been found to be more ergonomic than having it above the single-use portion, Another is that unit 1606 can be conveniently observed by several people and that it can be an otherwise standard workstation of hospital tower that has been programmed to interact with single-use portion 16400.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What is claimed is:

1. An endoscope with a side-mountable single-use portion and a multiple-use portion, wherein:
   the single-use portion includes:
      a housing that has a distal end and a proximal end and has a proximal port at said proximal end and an intermediate port distal to the proximal port;
      a cannula that extends distally from the distal end of the housing in an axial direction and has a distal port at a distal portion of the cannula;
      a single lumen extending from said proximal port at the proximal end of the housing to the distal port at the distal portion of the cannula;
      an imaging and illumination module at said distal portion of the cannula;
      an electrical connector that is affixed to said housing and is operatively coupled with said imaging and illumination module; and
   the multiple-use portion includes:
      a handle with a top, lateral side, and an open outwardly facing slot at the lateral side, which slot is elongated in the axial direction; and
      a display module mounted to the handle;
   wherein
      wherein one of said housing and said multiple-use portion includes at least one ridge and the other includes at least on slot, each of said at least one ridge and at least one slot are elongated in the axial direction, and said at least one ridge is configured to snap snugly but releasably into said at least one slot in a relative motion of the single-use portion and the reusable portion in a direction across the axial direction to thereby secure the single-use portion and the multiple-use portion to each other and thereby form said endoscope;
   wherein the electrical connectors of the housing and the reusable portion are configured to mate and establish an electrical contact between the single-use portion and the reusable portion in relative motion of the single-use portion and the reusable portion along the axial direction following the motion across the axial direction;
   wherein said electrical connectors when mated transmit power to said imaging and illumination module and transmit images therefrom to said display; and
   wherein said display nodule has a touch-sensitive screen that is above the single-use portion; and
   each of the proximal port, the intermediate port and the distal port connect to said single lumen.

2. The endoscope of claim 1, in which said proximal port protrudes proximally from said handle.

3. The endoscope of claim 1, in which said grooves and ridges extend to proximal ends of said housing and handle.

4. The endoscope of claim 1, in which the handle includes a WiFi circuit configured to wirelessly transmit images taken with said imaging and illumination module.

5. The endoscope of claim 1, in which said electrical connector in the reusable portion is configured for coupling to external equipment comprising one or more of monitors and/or workstations for sending thereto images taken with said imaging and illumination module.

6. The endoscope of claim 1, in which said display module is mounted on said handle for selective tilting and/or rotation relative to the handle about one or more axes.

7. The endoscope of claim 1, in which said proximal port is vertically in line with a center of said display module and less than 15 cm from a center of the display module, thereby placing the proximal port in a line and angle of sight of a viewer that includes both the display module and the proximal port.

8. An endoscopic multiple-use portion comprising:
   a multiple-use handle with a top, a lateral side, and a pistol grip configured for grasping with a user's hand;
   an open, outwardly facing slot at the lateral side of said handle, wherein said slot is above the pistol grip and extends along a longitudinal axis;
   wherein said slot is open in a direction transverse to said longitudinal axis, has a groove or a ride, and is configured for removably snap-fitting therein an insert housing that a proximally facing electrical contact and a ridge or a groove configured to snap to the groove or ridge in the slot when inserted in the slot in a direction across to said longitudinal axis;
   a distally facing electrical contact mounted on the handle and configured to make electrical contact with the proximally facing contact of the housing in a relative motion of the handle and the housing along said longitudinal axis subsequent to the motion acrtoss the longitudinal axis;
   a display module with a screen to display images, mounted to an upper portion of said handle for rotation and/or pivoting relative to the handle; and
   image processing circuits inside the handle, operatively coupled with said display module when said insert housing is snapped into said slot and configured to display images sent thereto from said imaging module.

9. The endoscopic apparatus of claim 8, including a lumen that extends essentially straight in said insert housing and cannula along said longitudinal axis and has a distal port extending proximally from a proximal end of the insert housing.

* * * * *